United States Patent
Kinoshita et al.

(10) Patent No.: US 7,056,311 B2
(45) Date of Patent: Jun. 6, 2006

(54) SANITARY NAPKIN

(75) Inventors: Masataka Kinoshita, Kagawa (JP); Kazuya Nishitani, Kagawa (JP); Toshiyuki Tanio, Kagawa (JP); Akane Sakai, Kagawa (JP); Jun Kudo, Kagawa (JP)

(73) Assignee: Uni-Charm Corporation, Shikokuchuo (JP)

( * ) Notice: Subject to any disclaimer, the term of this patent is extended or adjusted under 35 U.S.C. 154(b) by 20 days.

(21) Appl. No.: 10/841,363

(22) Filed: May 7, 2004

(65) Prior Publication Data

US 2004/0243087 A1 Dec. 2, 2004

(30) Foreign Application Priority Data

May 29, 2003 (JP) ............................. 2003-151999
Dec. 18, 2003 (JP) ............................. 2003-421580

(51) Int. Cl.
*A61F 13/20* (2006.01)

(52) U.S. Cl. ...................... 604/385.04; 604/385.03; 604/385.28

(58) Field of Classification Search ............ 604/387, 604/385.01, 385.03, 385.04, 385.28, 389
See application file for complete search history.

(56) References Cited

U.S. PATENT DOCUMENTS

| | | | |
|---|---|---|---|
| 5,221,275 A * | 6/1993 | Van Iten ................... 604/387 |
| 5,391,162 A * | 2/1995 | Widlund et al. ........ 604/385.04 |
| 5,423,787 A * | 6/1995 | Kjellberg ................ 604/368 |
| 5,439,458 A * | 8/1995 | Noel et al. .............. 604/378 |
| 5,591,148 A * | 1/1997 | McFall et al. ........... 604/378 |
| 6,168,582 B1 * | 1/2001 | Hasegawa ............. 604/385.02 |
| 6,312,418 B1 * | 11/2001 | Shimizu et al. ........ 604/385.02 |
| 6,375,645 B1 * | 4/2002 | Nishida et al. ........ 604/385.02 |
| 6,508,796 B1 | 1/2003 | Mizutani et al. |
| D474,273 S * | 5/2003 | Yamamoto .............. D24/125 |
| 6,569,140 B1 | 5/2003 | Mizutani et al. |
| 6,575,947 B1 * | 6/2003 | Tameishi et al. ....... 604/385.01 |
| 6,703,538 B1 * | 3/2004 | Lassen et al. ............ 604/378 |
| 6,911,574 B1 * | 6/2005 | Mizutani ................. 604/380 |
| 2002/0004654 A1 * | 1/2002 | Daniels et al. ........... 604/380 |
| 2003/0018314 A1 * | 1/2003 | Nozaki et al. .......... 604/385.101 |
| 2003/0055392 A1 * | 3/2003 | Tagami et al. ........... 604/378 |
| 2003/0100874 A1 * | 5/2003 | DeCarvalho et al. ... 604/380 |

(Continued)

FOREIGN PATENT DOCUMENTS

JP 6-501409 A1 2/1994

(Continued)

OTHER PUBLICATIONS

Tanio et al., U.S. Appl. No. 10/847,823, "Absorbent Article", filed May 17, 2004.

(Continued)

*Primary Examiner*—Tatyana Zalukaeva
*Assistant Examiner*—Ginger Chapman
(74) *Attorney, Agent, or Firm*—Darby & Darby

(57) ABSTRACT

Disclosed is a sanitary napkin which is effective in preventing liquid from leaking out obliquely rearward. The sanitary napkin has rear flaps rearward of fold-back flaps to be wrapped around a crotch part of an undergarment. The rear flap has a side edge substantially parallel to a longitudinal centerline. The rear flap is provided at its front portion with a rear pressure-sensitive adhesive layer. The rear pressure-sensitive adhesive layer is disposed forward of a rear end of a leakage preventing wall and a rear end of a main absorbent region. Since the rear flaps can be firmly fixed through the rear pressure-sensitive adhesive layers, the leakage preventing walls hardly move, so that the leakage preventing walls, as well as the rear flaps outside them, can effectively prevent obliquely rearward leakage.

15 Claims, 10 Drawing Sheets

U.S. PATENT DOCUMENTS

| | | | |
|---|---|---|---|
| 2004/0068244 A1* | 4/2004 | Salone et al. | 604/385.04 |
| 2004/0243082 A1* | 12/2004 | Kinoshita et al. | 604/380 |
| 2004/0249355 A1* | 12/2004 | Tanio et al. | 604/385.01 |
| 2004/0260262 A1* | 12/2004 | Nishitani et al. | 604/385.04 |
| 2004/0260263 A1* | 12/2004 | Tamagawa et al. | 604/385.04 |

FOREIGN PATENT DOCUMENTS

| | | |
|---|---|---|
| JP | 2000-189458 A1 | 7/2000 |
| JP | 2001-095842 A1 | 4/2001 |
| JP | 2002-330992 A1 | 11/2002 |
| JP | 2003-024376 A1 | 1/2003 |
| JP | 2003-052744 A1 | 2/2003 |
| JP | 2003-062008 A1 | 3/2003 |
| JP | 2003-339764 A1 | 12/2003 |
| WO | WO 01/72254 A2 * | 10/2001 |

OTHER PUBLICATIONS

Tamagawa et al., U.S. Appl. No. 10/862,928, "Sanitary Napkin", filed Jun. 7, 2004.

Nishitani et al., U.S. Appl. No. 10/862,926, "Sanitary Napkin", filed Jun. 7, 2004.

* cited by examiner

SANITARY NAPKIN

BACKGROUND OF THE INVENTION

1. Field of the Invention

The present invention relates to a sanitary napkin suitable for nighttime use. More particularly, the invention relates to a sanitary napkin provided with rear flaps for widely covering a posterior part of the crotch and the buttocks.

2. Description of the Related Art

Sanitary napkins suitable for nighttime use are typically constructed to include an elongated main body and front fold-back flaps and rear flaps projecting outward from transversely opposite sides of the main body.

Japanese Unexamined Patent Publication No. 2001-95842 (Patent Publication 1) discloses a sanitary napkin, wherein a narrowest portion where the width of the napkin is smallest is disposed rearward of the fold-back flaps but forward of the rear flaps. The rear flaps are shaped such that the width of the napkin gradually increases rearward from the narrowest portion, reaches a widest portion, and gradually decreases from the widest portion to a rear end edge of the napkin. Here, the rear flaps have edges shaped arcuately to project transversely outward, and the widest portion is substantially at a longitudinal center of the rear flap.

On the skin-side surface of the sanitary napkin disclosed in Patent Publication 1, gathered cuffs are disposed to extend longitudinally at both sides of its longitudinal centerline. These gathered cuffs exhibit an elastic contractive force for longitudinal contraction and are allowed to rise from the skin-side surface due to the elastic contractive force. The gathered cuffs extend from a region located between the fold-back flaps to a region located between front halves of the rear flaps, wherein rear ends of the gathered cuffs are substantially at the same position as the widest portion.

In the sanitary napkin disclosed in Patent Publication 1, the rear flaps are aimed at eliminating worries about rearward leakage of liquid, and the gathered cuffs interposed between the wearer's skin and the skin-side surface of the sanitary napkin are aimed at further eliminating worries about leakage of liquid.

On the other hand, Japanese Unexamined Patent Publication No. 2002-330992 (Patent Publication 2) discloses a sanitary napkin, wherein front wings project outward from transversely opposite sides of a main body and larger rear-side wings, which are disposed rearward of the front wings, also project outward from the transversely opposite sides. The rear-sidewings have fold-back portions extending alongside the front wings.

When the sanitary napkin disclosed in Patent Publication 2 is to be put on, the front wings are folded back against and adhered to an outer surface of an undergarment at a crotch part thereof. Subsequently,the rear-side wings are placed on a lower part of a back body of the undergarment, wherein the fold-back portions projecting into leg openings of the undergarment are folded back against and adhered to the outer surface of the undergarment. Thus, the sanitary napkin can be put on along with the undergarment.

When the elongated sanitary napkin disclosed in Patent Publication 1 is applied to the wearer's body, the skin-side surface may contact the vaginal opening (menstrual blood discharging part) at a position between longitudinal centers of the front fold-back flaps and face the anus at a position near the narrowest portion. Here, the rear flaps, which are placed on a lower part of a back body of an undergarment, may be curved to conform to the surface shape of the wearer's buttocks. Moreover, the rear flaps located rearward of the anus-facing portion may not project into leg openings of the undergarment.

In the sanitary napkin disclosed in Patent Publication 1, however, the rear flap has the arcuate edge over its entire length, wherein the widest portion is substantially at the same position as the longitudinal center of the rear flap and at a considerable distance rearward from the fold-back flap. Furthermore, the rear flap has a width gradually increasing from the narrowest portion behind the fold-back flap to the widest portion. That is, the front portion of the rear flap is of a small area.

In such a front portion of the rear flap, heretofore, it has been difficult to dispose a pressure-sensitive adhesive layer for adhering the rear flap to an undergarment; in the conventional sanitary napkins, therefore, the pressure-sensitive adhesive layer has been disposed only centrally of the rear flap.

When the sanitary napkin is worn, however, central and rear portions of the sanitary napkin subjected to a tightening force of the undergarment try to fit in the cleft of the buttocks, so that the front portions of the rear flaps tend to move away from the undergarment due to deformation of liquid absorbent layer. In addition, the front portions of the rear flaps tend to be drawn toward the cleft of the buttocks in conjunction with the deformation of liquid absorbent layer.

If the front portions of the rear flaps tend to move freely, as set forth above, the gathered cuffs inside them tend to come closer to the longitudinal centerline, substantially decreasing an area of the skin-side surface between these gathered cuffs. If the gathered cuffs fall inward, additionally, the exposed area of the skin-side surface will be much smaller. Accordingly, menstrual blood trying to flow from the anus to the buttocks may be directly given not only to the skin-side surface but also to the gathered cuffs. Moreover, the menstrual blood may easily migrate to the small front portions of the rear flaps beyond the gathered cuffs, flowing out of the front portions to reach the undergarment.

When a wearer lies on her back during sleep, on the other hand, the rear portion of the sanitary napkin may be flattened by the buttocks, so that a portion located between the front portions of the rear flaps may easily move away from the wearer's body with a bending force concentrated therein. At this portion, accordingly, the gathered cuffs need be raised high. However, since the front portions of the rear flaps are allowed to move freely at both sides of this portion as set forth above, the gather cuffs tend to come closer to the center. Furthermore, such high gathered cuffs tend to fall to cover the skin-side surface. As a result, menstrual blood can easily reach the undergarment beyond the front portions of the rear flaps, as set forth above.

Compared with the sanitary napkin disclosed Patent Publication 1, the sanitary napkin disclosed in Patent Publication 2 can be firmly fixed to the undergarment due to the presence of the fold-back portions of the rear-side wings. In this sanitary napkin, however, since four separate portions (the front wings and the fold-back portions of the rear-side wings) need be folded back against and adhered to the outer surface of the undergarment, the sanitary napkin will be troublesome to put on. In addition, it is difficult to hold the sanitary napkin in proper position with respect to the crotch part of the undergarment until the fixing procedure is completed. Furthermore, once the fixing procedure is completed, it will be extremely troublesome to change the position of the sanitary napkin.

SUMMARY OF THE INVENTION

The present invention has been worked out in view of the shortcomings in the prior art set forth above. It is therefore an object of the present invention to provide a sanitary napkin in which front portions of rear flaps can be firmly fixed to an undergarment as well as liquid given to leakage preventing walls can be effectively prevented from leaking out of the sanitary napkin.

According to the present invention, there is provided a sanitary napkin comprising:

an elongated main body having a skin-side surface and a garment-side surface and including a liquid absorbent layer for absorbing liquid applied to the skin-side surface and a backsheet appearing on the garment-side surface;

fold-back flaps intended to be folded back against an outer surface of an undergarment at a crotch part thereof in use, the fold-back flaps projecting outward from transversely opposite sides of the main body and having front pressure-sensitive adhesive layers on garment-side surfaces thereof for adhering the fold-back flaps to the outer surface of the undergarment;

rear flaps intended to be placed on an inner surface of the undergarment in use in an unfolded state, the rear flaps projecting outward from the transversely opposite sides of the main body and having rear pressure-sensitive adhesive layers on garment-side surfaces thereof for adhering the rear flaps to the inner surface of the undergarment, the rear flaps being located rearward of the fold-back flaps and larger in length than the fold-back flaps; and longitudinally extending leakage preventing walls disposed on the skin-side surface of the main body and at equal distances on each side of a longitudinal centerline, each leakage preventing wall having front and rear ends fixed to the skin-side surface and exhibiting an elastic contractive force to bring the front and rear ends closer to each other so as to rise from the skin-side surface, wherein the rear pressure-sensitive adhesive layers are located forward of the rear ends of the leakage preventing walls.

In the sanitary napkin of the present invention, the rear flap can be firmly fixed to the inner surface of the undergarment at a position forward of the rear end of the leakage preventing wall. Accordingly, even if the liquid absorbent layer is deformed to have the skin-side surface of the main body fit in the cleft of the buttocks, the front portions of the rear flaps may hardly move away from the undergarment and the distance between the leakage preventing walls may be maintained, so that menstrual blood flowing posteriorly down the wearer's body can be effectively received by the skin-side surface of the main body. Moreover, even if menstrual blood is directly given to the leakage preventing walls, the large rear flaps outside the leakage preventing walls can effectively prevent the liquid from leaking out obliquely rearward.

On each side of the longitudinal centerline, preferably, a front end of the rear pressure-sensitive adhesive layer is at a distance of equal to or greater than 10 mm forward of the rear end of the leakage preventing wall. With the front end of the rear pressure-sensitive adhesive layer being thus located, the distance between the leakage preventing walls can be maintained while keeping the front portions of the rear flaps firmly fixed to the inner surface of the undergarment.

On each side of the longitudinal centerline, the sanitary napkin of the present invention may be constructed such that a starting point from which a half-width, measured from the longitudinal centerline to a side edge, starts to increase rearward is located rearward of the fold-back flap, and the rear flap includes: a front spreading portion where the half-width gradually increases rearward from the starting point; an intermediate portion where the side edge extends parallel to the longitudinal centerline or extends with a deviation within a range of ±5 mm transversely from an imaginary line parallel to the longitudinal centerline; and a rear converging portion where the half-width gradually decreases toward a rear end edge of the napkin. Here, a front boundary point between the front spreading portion and the intermediate portion may be located forward of the rear end of the leakage preventing wall. Preferably, the front boundary point is at a distance of equal to or greater than 30 mm forward of the rear end of the leakage preventing wall. In this construction, since the wide intermediate portion extends alongside a rear portion of the leakage preventing wall, the rear pressure-sensitive adhesive layer may be made large enough to firmly fix the rear flap to the inner surface of the undergarment. In addition, even if menstrual blood is directly given to the leakage preventing wall to reach the rear flap, the menstrual blood can be effectively prevented from leaking out.

In the present invention, $L1/L0$ is preferably at least ⅓, where $L0$ represents a length from the starting point to the rear end edge of the napkin while $L1$ represents a length from the front boundary point to a rear boundary point between the intermediate portion and the rear converging portion. In this case, $L1$ preferably falls within the range of 60 to 200 mm. With $L1$ being set within the foregoing range, leakage in the transverse direction can more effectively be prevented by the rear flap.

In the present invention, an imaginary line, which coincides with the starting point and is tangent to an edge of the rear flap, preferably forms an angle of 30 to 45 degrees with the longitudinal centerline. With this construction, the edge of the rear flap at the front spreading portion may easily conform to the curved surface of the wearer's thigh without projecting into the leg opening of the undergarment. Moreover, it can make it easy to increase $L1$.

In the present invention, preferably, both a width from a rising base of the leakage preventing wall to the front boundary point and a width from the rising base to the rear boundary point fall within the range of 30 to 70 mm. Also preferably, a length from a transverse reference line, which longitudinally bisects the fold-back flap, to the front boundary point falls within the range of 80 to 150 mm.

In the present invention, the skin-side surface of the main body may have an elongated main absorption region surrounded by a compressed groove in a region between the leakage preventing walls, and the front boundary point may be at a distance of equal to or greater than 30 mm forward of a rear end of the main absorption region.

In the present invention, auxiliary pressure-sensitive adhesive layers (or second rear pressure-sensitive adhesive layers) may further be disposed on the garment-side surfaces of the rear flaps at a distance rearward of the rear pressure-sensitive adhesive layers (or first rear pressure-sensitive adhesive layers). On each side of the longitudinal centerline, furthermore, a front end of the rear pressure-sensitive adhesive layer may be located forward of the front boundary point, and a rear end of the auxiliary pressure-sensitive adhesive layer may be located rearward of the rear boundary point. With this construction, the rear flap at both the front and rear portions may be firmly fixed to the inner surface of the undergarment.

In the present invention, preferably, the individual rear flaps are allowed to be folded back against the skin-side surface of the main body and the main body is also allowed to be folded, with the skin-side surface directed inward, on a transversely extending folding boundary line coinciding with a midpoint between the front boundary point and the rear boundary point, wherein the folding boundary line crosses none of the pressure-sensitive adhesive layers, and when the individual rear flaps are folded back and the main body is subsequently folded on the folding boundary line, the rear pressure-sensitive adhesive layers confront the auxiliary pressure-sensitive adhesive layers. With this construction, the sanitary napkin can be compactly folded for disposal after use, wherein since the rear pressure-sensitive adhesive layers may be adhered to the auxiliary pressure-sensitive adhesive layers, the sanitary napkin can be certainly kept in the compactly folded state.

In the present invention, a half-width, measured from the longitudinal centerline to a side edge, may be larger in a rear portion of the rear flap than in a front portion of the rear flap, and may be largest rearward of a longitudinal center of the rear flap. In this construction, preferably, $Le/L0$ is at most $\frac{1}{5}$, where $Le$ represents a length from a point where the half-width is largest to a rear end edge of the napkin while $L0$ represents a length of the rear flap. Also in this construction, auxiliary pressure-sensitive adhesive layers may further be disposed on the garment-side surfaces of the rear flaps at a distance rearward of the rear pressure-sensitive adhesive layers, wherein the auxiliary pressure-sensitive adhesive layers are farther away from the longitudinal centerline than is the rear pressure-sensitive adhesive layers. If the rear flaps have their widest portions near the rear end edge of the napkin, the rear flaps can be placed on the back body of the undergarment in a widely opened state by pulling up them obliquely upwardly, while preventing the occurrence of displacement.

BRIEF DESCRIPTION OF THE DRAWINGS

The present invention will be understood more fully from the detailed description given hereinafter and from the accompanying drawings of the preferred embodiments of the present invention, which, however, should not be taken to limit to the invention, but are for explanation and understanding only.

In the drawings.

DESCRIPTION OF THE PREFERRED EMBODIMENT

The present invention will be discussed hereinafter in detail in terms of the preferred embodiments according to the present invention with reference to the accompanying drawings. In the following description, numerous specific details are set forth in order to provide a thorough understanding of the present invention. It will be obvious, however, to those skilled in the art that the present invention may be practiced without these specific details. In other instances, well-known structures are not shown in detail in order not to obscure the features of the present invention.

It should be noted that the sanitary napkin, as well as its individual components, has two major surfaces: of which one surface intended to be worn toward the wearer's crotch is referred to as "skin-side surface", while the other surface is referred to as "garment-side surface". It should also be noted that unless otherwise stated, the term "length" as used herein refers to a dimension measured longitudinally of the sanitary napkin and the term "width" as used herein refers to a dimension measured transversely of the sanitary napkin.

Figure 1:
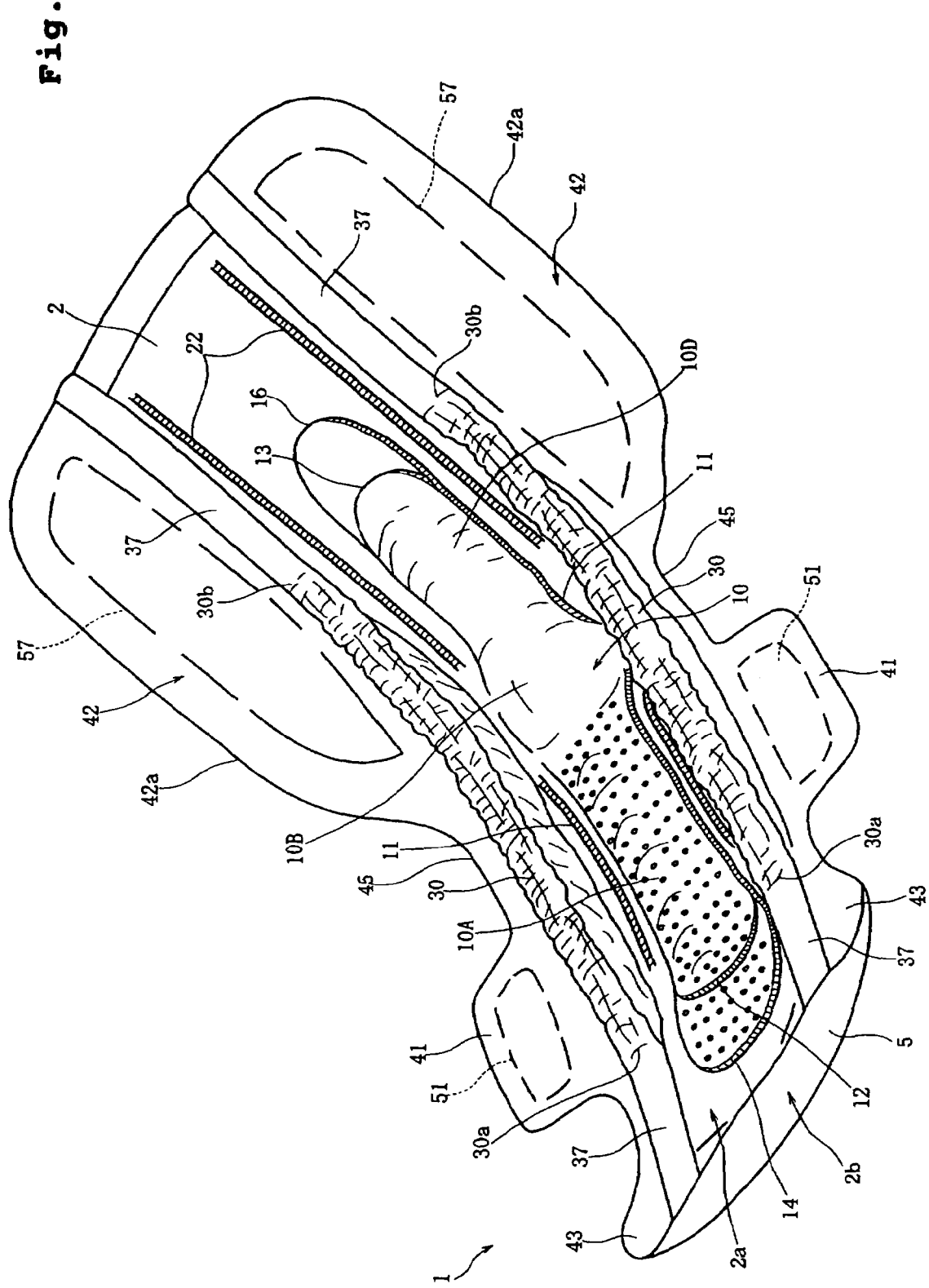
FIG. 1 is a perspective view of a sanitary napkin according to a first embodiment of the present invention.
Figure 2:
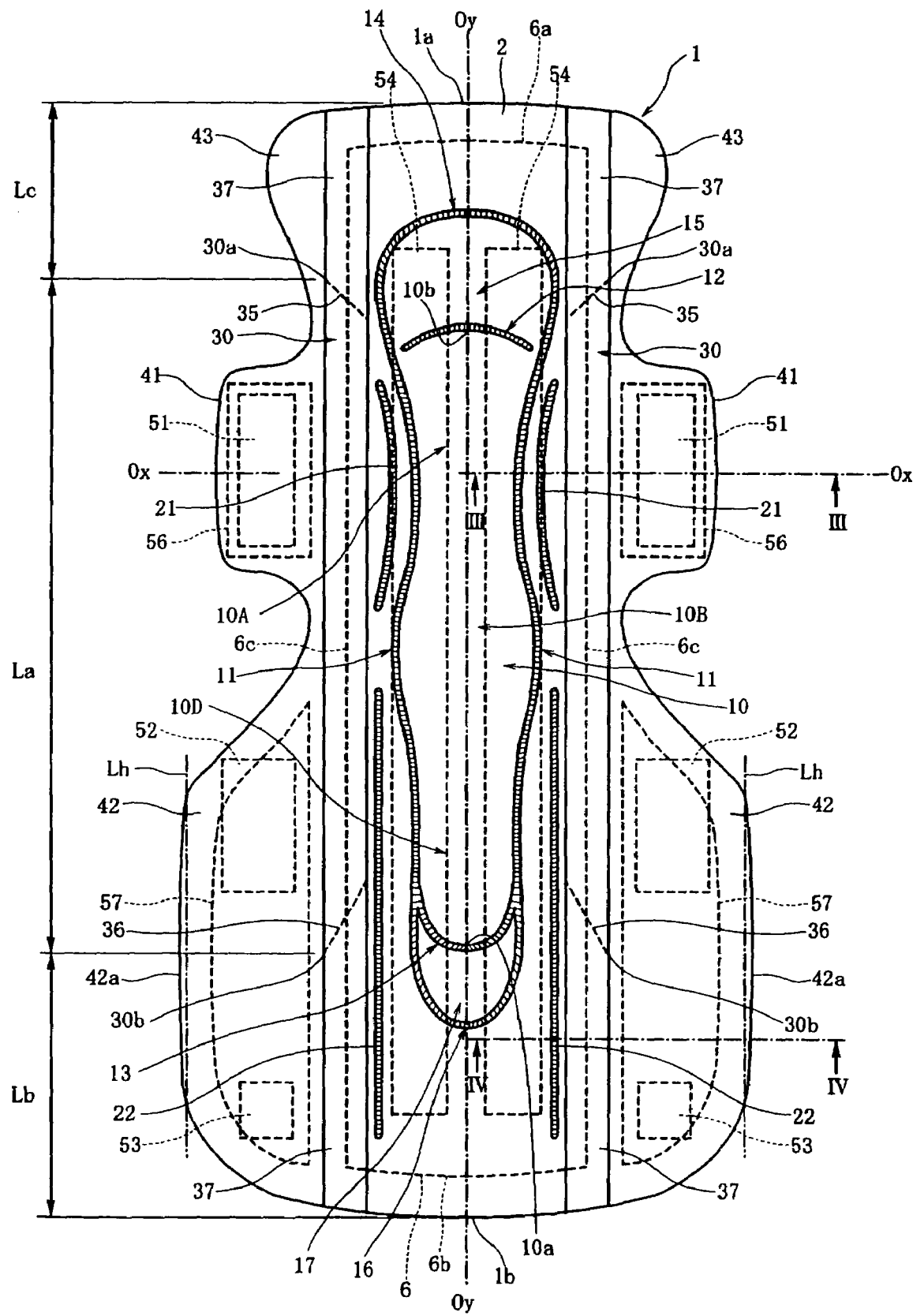
FIG. 2 is a top plan view of the sanitary napkin according to the first embodiment.
Figure 3:
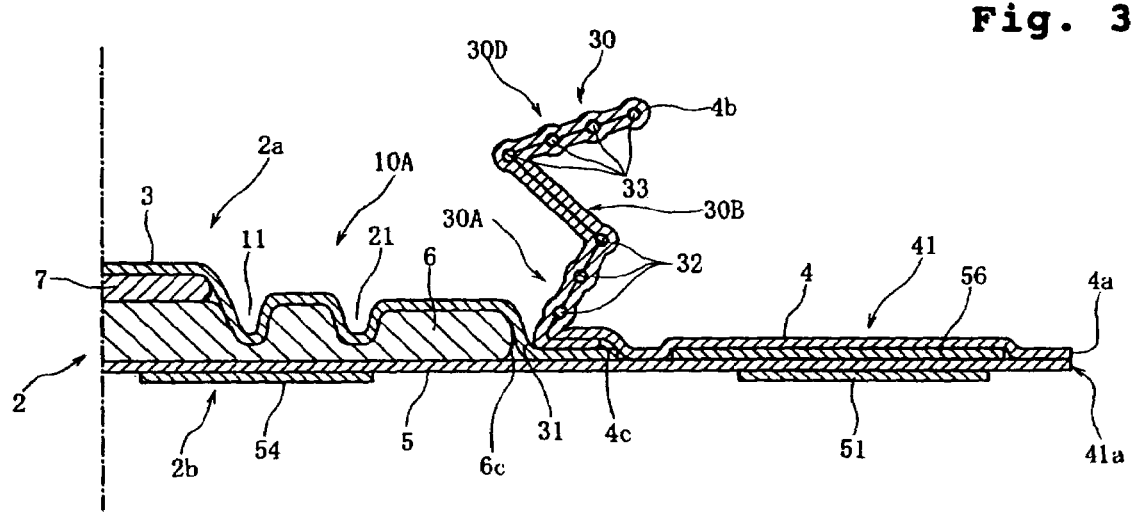
FIG. 3 is a half sectional view taken along line III—III of FIG. 2.
Figure 4:
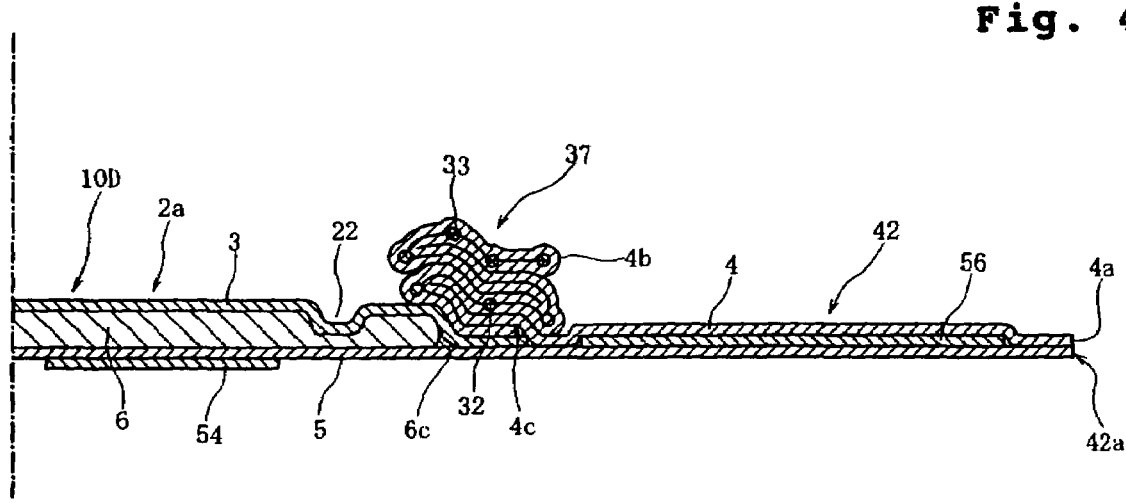
FIG. 4 is a half sectional view taken along line IV—IV of FIG. 2.
Figure 5:
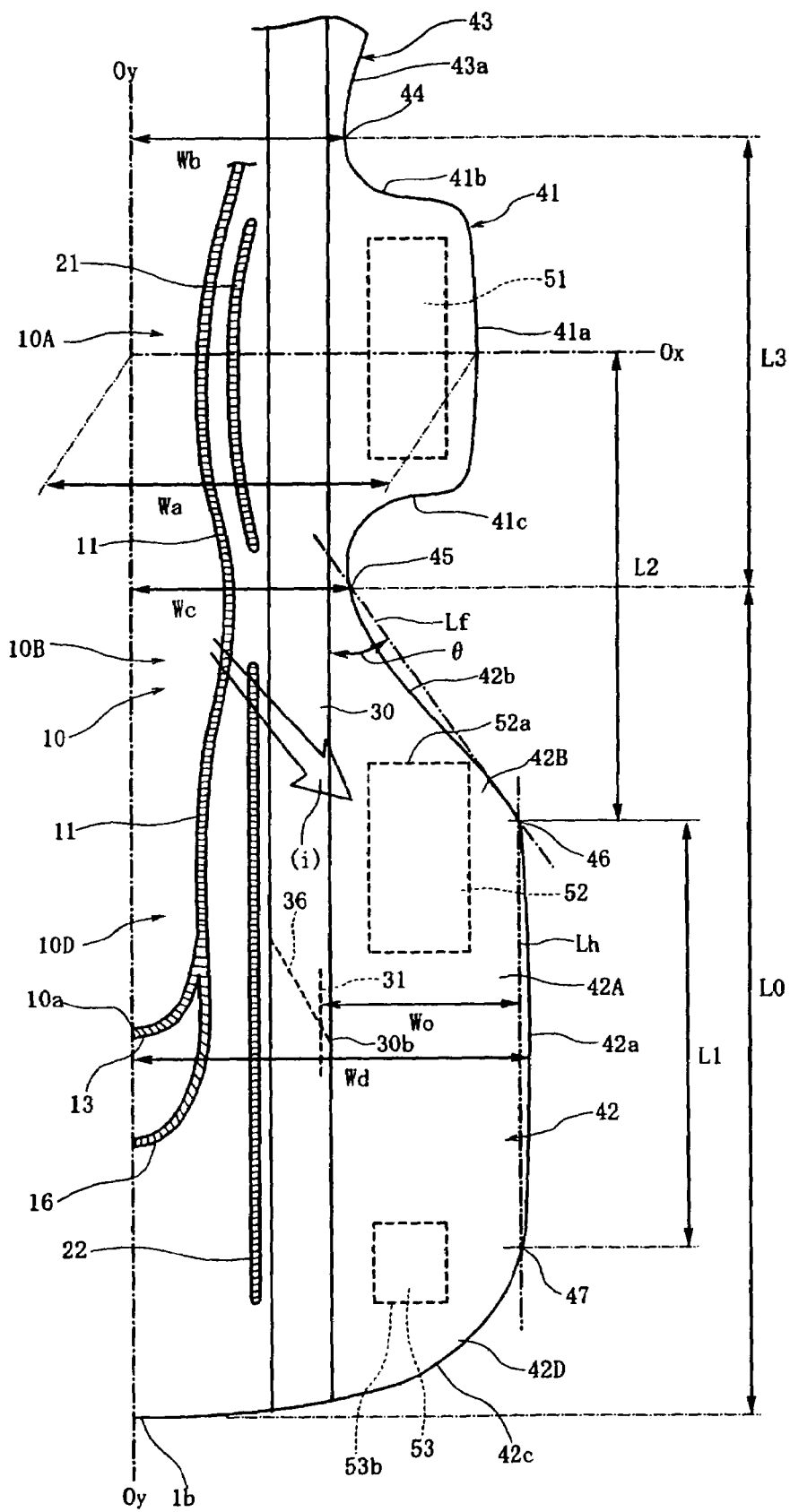
FIG. 5 is a top plan view for description of the shapes of flaps.

FIG. 1 is a perspective view of a sanitary napkin 1 according to a first embodiment of the present invention; FIG. 2 is a top plan view of the sanitary napkin 1; FIG. 3 is a half sectional view taken along line III—III of FIG. 2; FIG. 4 is a half sectional view taken along line IV—IV of FIG. 2; and FIG. 5 is a top plan view for description of the shapes of flaps.

According to the first embodiment shown in FIGS. 1–5, the sanitary napkin 1 comprises: an elongated main body 2 having a skin-side surface 2a and a garment-side surface 2b; and a pair of leakage preventing walls 30, 30 that are allowed to rise from the skin-side surface 2a of the main body 2.

In FIG. 2, the sanitary napkin 1, which is slightly curved in FIG. 1, is shown in a fully opened (or flattened) state. FIG. 2 shows a longitudinal centerline Oy—Oy coinciding with midpoints of front and rear end edges 1a, 1b of the sanitary napkin 1, wherein the sanitary napkin 1 has bilateral symmetry about the longitudinal centerline Oy—Oy. FIG. 2 also shows a transverse reference line Ox—Ox perpendicular to the longitudinal centerline Oy—Oy. The sanitary napkin 1 is intended to be worn with the skin-side surface 2a facing the crotch of a woman so that the woman's vaginal opening faces the intersection between the longitudinal centerline Oy—Oy and the transverse reference line Ox—Ox and its surrounding area.

As shown in FIGS. 3 and 4, a liquid-permeable topsheet 3 appears on the skin-side surface 2a of the main body 2, in a region between the leakage preventing walls 30, 30; a side sheet 4 appears outside each leakage preventing wall 30. In the present embodiment, the side sheet 4 forms the leakage preventing wall 30. On the other hand, a liquid-impermeable backsheet 5 appears on the garment-side surface 2b of the main body 2.

In the region between the leakage preventing walls 30, 30, the main body 2 has a liquid absorbent layer 6 disposed between the topsheet 3 and the backsheet 5. As shown in FIG. 2, the liquid absorbent layer 6 is of an almost rectangular shape. The liquid absorbent layer 6 has a front end edge 6a slightly inside the front end edge 1a of the sanitary napkin 1 and a rear end edge 6b slightly inside the rear end edge 1b of the sanitary napkin 1. The liquid absorbent layer 6 has transversely opposite side edges 6c inside rising bases 31 of the leakage preventing walls 30.

In the skin-side surface 2a, compressed grooves where the topsheet 3 and the liquid absorbent layer 6 are compressed are formed in the region between the leakage preventing walls 30, 30. The compressed grooves comprise: longitudinal compressed grooves 11, 11 extending longitudinally in a curved manner; a front transverse compressed groove 12 located between front portions of the longitudinal compressed grooves 11, 11; and a rear transverse compressed groove 13 connecting rear portions of the longitudinal compressed grooves 11, 11.

The region surrounded by the longitudinal compressed grooves 11, 11, the front transverse compressed groove 12, and the rear transverse compressed groove 13 is referred to as elongated main absorbent region 10. The main absorbent region 10 includes a front main absorbent region 10A, an intermediate main absorbent region 10B, and a rear main absorbent region 10D.

In the front main absorbent region 10A, the right and left longitudinal compressed grooves 11, 11 are curved toward the longitudinal centerline Oy—Oy, wherein the distance between the longitudinal compressed grooves 11, 11 is smallest on the transverse reference line Ox—Ox. In the intermediate main absorbent region 10B, the longitudinal compressed grooves 11, 11 are curved away from the longitudinal centerline Oy—Oy. The rear main absorbent region 10D is elongated longitudinally of the napkin, in which the distance between the longitudinal compressed grooves 11, 11 is smaller than in the intermediate main absorbent region 10B.

In the main absorbent region 10, a bulky, liquid permeable layer (cushion layer) 7 of a lower density than the liquid absorbent layer 6 is disposed between the topsheet 3 and the liquid absorbent layer 6, as shown in FIG. 3. As a result, the skin-side surface 2a of the main body 2 is raised more in the main absorbent region 10 than in the surrounding region, as shown in FIG. 1.

Forward of the front transverse compressed groove 12 is provided a front outside compressed groove 14, as shown in FIG. 2. The front outside compressed groove 14 is curved forward and connects the right and left longitudinal compressed grooves 11, 11. The region surrounded by the front transverse compressed groove 12 and the front outside compressed groove 14 is referred to as front auxiliary absorbent region 15.

Rearward of the rear transverse compressed groove 13 is provided a rear outside compressed groove 16. The longitudinal compressed grooves 11, 11, the rear transverse compressed groove 13, and the rear outside compressed groove 16 are connected together, and both the rear transverse compressed groove 13 and the rear outside compressed groove 16 are curved rearward. Here, the region surrounded by the rear transverse compressed groove 13 and the rear outside compressed groove 16 is referred to as rear auxiliary absorbent region 17.

On both right and left sides of the front main absorbent region 10A, first outside longitudinal compressed grooves 21, 21 are provided outside and at a distance apart from the longitudinal compressed grooves 11, 11. The first outside longitudinal compressed grooves 21, 21 are also curved toward the longitudinal centerline Oy—Oy, wherein the distance therebetween is smallest on the transverse reference line Ox—Ox.

On both right and left sides of the rear main absorbent region 10D, furthermore, second outside longitudinal compressed grooves 22, 22 are provided at a distance transversely apart from the longitudinal compressed grooves 11, 11. The second outside longitudinal compressed grooves 22, 22 extend longitudinally in substantially parallel relation to the longitudinal centerline Oy—Oy. It should be noted that they extend rearward from a boundary between the intermediate main absorbent region 10B and the rear main absorbent region 10D to have their rear ends farther rearward of the rear outside compressed groove 16.

The individual compressed grooves are formed by heating the topsheet 3 and the liquid absorbent layer 6 under pressure from the side of the topsheet 3. At the bottoms of the individual compressed grooves, high-density compressed portions (highly compressed portions) and medium-density compressed portions (portions whose density is slightly lower than the high-density compressed portions) alternate with each other along the linear pattern of the compressed grooves so that the grooves are of a sufficient depth overall. The individual compressed grooves may be replaced by dot-like compressed portions arranged along the linear pattern at spaced intervals.

As shown in FIGS. 3 and 4, the side sheet 4 has an edge 4a coinciding with the outer edge of the backsheet 5. The side sheet 4 has a single-layer portion and a multi-layer portion, wherein the single-layer portion is bonded to the backsheet 5 or other materials disposed on the backsheet 5, whereas the multi-layer portion forms the leakage preventing wall 30 (see FIG. 3) or a stacked/fixed portion 37 (see FIG. 4). In the multi-layer portion, at first, the side sheet 4 is folded on its fold line 4b to have an edge 4c on the topsheet 3. In FIG. 3, the side sheet 4 is bonded to the topsheet 3 from the rising base 31 to the edge 4c.

Confronting surfaces of the side sheet 4 thus folded in two are bonded together through a hot-melt type adhesive with a plurality of elastic members 32, 33 disposed therebetween. The individual elastic members 32, 33 extend longitudinally over the entire length of the leakage preventing wall 30 and beyond the front and rear ends 30a, 30b. The elastic members 32, 33 are bonded to the side sheet 4 while being longitudinally stretched to a predetermined degree.

In an area of a length Lb from a rear bond edge 36 to the rear end edge 1b (see FIG. 2), the multi-layer portion of the side sheet 4 previously folded in two is further folded in three, as shown in FIG. 4, wherein these layers are bonded to each other as well as to the topsheet 3, thereby forming the stacked/fixed portion 37. Also in an area of a length Lc from a front bond edge 35 to the front end edge 1a, the multi-layer portion of the side sheet 4 is similarly folded and bonded, forming the stacked/fixed portion 37.

The front bond edge 35 and the rear bond edge 36 extend obliquely with respect to both the longitudinal direction and the transverse direction. Between the front bond edge 35 and the rear bond edge 36, the multi-layer portion of the side sheet 4 previously folded in two forms the leakage preventing wall 30 that can rise from the skin-side surface 2a, as shown in FIG. 3. It should be noted that the front end 30a of the leakage preventing wall 30 refers to one end of the front bond edge 35 that is closer to the front end edge 1a, and the rear end 30b of the leakage preventing wall 30 refers to one end of the rear bond edge 36 that is closer to the rear end edge 1b. The length of the leakage preventing wall 30 refers to a dimension La from the front end 30a to the rear end 30b.

The elastic members 32, 33 exert an elastic contractive force between the front end 30a and the rear end 30b, so that an elastic force acts to bring the front end 30a and the rear end 30b closer to each other, whereby the main body 2 is curved as shown in FIG. 1 and each leakage preventing wall 30 is raised from the skin-side surface 2a between the front end 30a and the rear end 30b.

Because the side sheet 4 at the stacked/fixed portion 37 is folded in a multi-layer structure and then bonded and fixed as shown in FIG. 4, the leakage preventing wall 30 includes: a lower inclined panel 30A extending obliquely upward from the rising base 31 toward the outside; an intermediate inclined panel 30B extending obliquely upward from the upper end of the lower inclined panel 30A toward the longitudinal centerline Oy—Oy; and a skin-contacting panel 30D extending obliquely upward from the upper end of the intermediate inclined panel 30B toward the outside, as shown in the half sectional view of FIG. 3.

Next, the sanitary napkin 1 will be described with respect to the shape of each side edge.

Along the transverse reference line Ox—Ox, fold-back flaps 41 are disposed to project transversely outward from the main body 2. Each fold-back flap 41 extends over a given length with center at the transverse reference line Ox—Ox. Rearward of the fold-back flaps 41 are disposed rear flaps 42 also projecting transversely outward from the main body 2; forward of the fold-back flaps 41 are disposed front flaps 43 projecting transversely outward from the main body 2. Since the sanitary napkin 1 has bilateral symmetry about the longitudinal centerline Oy—Oy, the right and left flaps are of symmetrical shape.

In FIG. 5, the flaps are illustrated on an enlarged scale.

As used herein, the term "half-width" refers to a dimension measured transversely from the longitudinal centerline Oy—Oy to one side edge of the sanitary napkin 1.

The half-width from the longitudinal centerline Oy—Oy to a side edge 41a of the fold-back flap 41 is largest on the transverse reference line Ox—Ox, wherein Wa designates the largest half-width within an area of a length L3. The side edge 41a is generally parallel to the longitudinal centerline Oy—Oy so as to provide an almost constant half-width over a given length of the side edge 41a. Between the fold-back flap 41 and the front flap 43 is provided a first narrowest portion of a smallest half-width Wb. At the first narrowest portion, the napkin's edge provides a first starting point 44. The fold-back flap 41 has a front edge 41b that is curved to gradually increase the half-width rearward from the first starting point 44 and continue to the side edge 41a.

The edge of the sanitary napkin 1 is also curved to gradually increase the half-width forward from the first starting point 44, providing the front flap 43 that projects transversely outward.

Between the fold-back flap 41 and the rear flap 42 is provided a second narrowest portion of a smallest half-width Wc. At the second narrowest portion, the napkin's edge provides a second starting point 45. The fold-back flap 41 has a rear edge 41c that is curved to gradually decrease the half-width rearward from the side edge 41a.

The rear flap 42 extends from the second starting point 45 to the rear end edge 1b of the sanitary napkin 1. The rear flap 42 may be divided in three areas: an intermediate portion 42A; a front spreading portion 42B; and a rear converging portion 42D.

In the intermediate portion 42A of a length L1, the half-width is almost. constant. That is, the intermediate portion 42A has a side edge 42a substantially parallel to the longitudinal centerline Oy—Oy.

Here "substantially parallel to the longitudinal centerline Oy—Oy" means that the side edge 42a extends with a deviation within a range of ±5 mm (preferably ±3 mm) transversely from an imaginary parallel line Lh parallel to the longitudinal centerline Oy—Oy.

In the present embodiment in which the side edge 42a is slightly curved outward as shown in FIG. 5, therefore, the side edge 42a extends outside the imaginary parallel line Lh but without deviation of greater than 5 mm therefrom. Of course, the side edge 42a may be parallel to the longitudinal centerline Oy—Oy without any deviation. The side edge 42a may also extend in the form of a wavy line to have an outwardly curved portion and an inwardly curved portion or extend in the form of a zigzag line. In these cases, the side edge 42a extends without deviation of greater than 5 mm (preferably 3 mm) outward from the imaginary parallel line Lh and without deviation of greater than 5 mm (preferably 3 mm) inward from the imaginary parallel line Lh.

In the rear flap 42, the front end of the side edge 42a is referred to as front boundary point 46 and the rear end is referred to as rear boundary point 47. More specifically, the front and rear boundary points 46, 47 are front and rear intersections between the imaginary parallel line Lh and the napkin's edge, respectively.

The front spreading portion 42B extends from the second starting point 45 to the front boundary point 46. The front spreading portion 42B has an edge 42b that is curved to gradually increase the half-width rearward from the second starting point 45 to the front boundary point 46.

On the other hand, the rear converging portion 42D has an edge 42c that is curved to gradually decrease the half-width rearward from the rear boundary point 47 to the rear end edge 1b. The edge 42c is curved obliquely rearward. The radius of curvature of the edge 42c of the rear converging portion 42D is smaller than that of the edge 42b of the front spreading portion 42B.

In the present embodiment in which the side edge 42a is substantially parallel to the longitudinal centerline Oy—Oy over the length L1, the rear flap 42 has an appropriate width although extending over a large area. Hereinbelow, preferred dimensions of the individual portions, as well as dimensional relationships between the portions, will be described.

The half-width Wb at the first starting point 44 located forward of the fold-back flap 41 is almost equal to the half-width Wc at the second starting point 45 located rearward of the fold-back flap 41.

When an imaginary tangent line Lf is drawn to coincide with the second starting point 45 and to be tangent to the edge of the rear flap 42, the imaginary tangent line Lf preferably forms an angle θ of 30–45 degrees with the longitudinal centerline Oy—Oy. Also when another imaginary tangent line is drawn to coincide with the first starting point 44 and to be tangent to the edge of the front flap 43, this imaginary tangent line preferably forms an angle of 30–45 degrees with the longitudinal centerline Oy—Oy. With the angles being set within the foregoing range, both the edge 42b of the front spreading portion 42B of the rear flap 42 and the side edge 43a of the front flap 43 may extend along the edge of the leg opening of the undergarment when the sanitary napkin 1 is put on with the transverse reference line Ox—Ox coinciding with both the longitudinal center of the crotch part of the undergarment and the center of the wearer's vaginal opening, so that the edge 42b and the side edge 43a can be prevented from projecting far into the leg opening.

Preferably, a length L2 from the transverse reference line Ox—Ox to the front boundary point 46 falls within the range of 80 to 150 mm. With the length L2 and the angle θ being set within the foregoing ranges, the rear flap 42 may hardly project into the leg opening of the undergarment while the length L1 of the side edge 42a can be made sufficiently long.

The rear flap 42 has a length L0 from the second starting point 45 to the rear end edge 1c. The length L0 is at least twice the length of the fold-back flap 41, i.e., at least twice the length L3 from the first starting point 44 to the second starting point 45. Here, the rear flap 42 provides a largest half-width Wd that is equal to or greater than the largest half-width Wa within the area of the length L3.

The distance between the rising base 31 of the leakage preventing wall 30 and the front and rear boundary points 46, 47, i.e., width W0 from the rising base 31 to the imaginary parallel line Lh, falls within the range of 30 to 70 mm. Here, the distance between the rising bases 31 of the right and left leakage preventing walls 30 preferably falls within the range of 60 to 120 mm. If it is below the range, the area intended to receive menstrual blood may be too small; if it is above the range, the width of the sanitary napkin 1 may be too large. Accordingly, the half-width at the front and rear boundary points 46, 47, i.e., the half-width at the imaginary parallel line Lh, may fall within the range of 60 to 130 mm.

The length L1 of the intermediate portion 42A of the rear flap 42 from the front boundary point 46 to the rear boundary point 47 is at least ⅓, preferably at least ½, of the length L0 from the second starting point 45 to the rear end edge 1b. The length L1 preferably falls within the range of 60 to 200 mm. With the width W0 and the length L1 being set within the foregoing ranges, the intermediate portion 42A of an almost constant width may be elongated longitudinally of the napkin, so that the area of the rear flap 42 may be increased without extremely projecting transversely outward.

The front boundary point 46 is located forward of the rear end 30b of the leakage preventing wall 30. Preferably, the longitudinal distance between the front boundary point 46 and the rear end 30b is equal to or greater than 30 mm. It is also preferred that the rear end 30b of the leakage preventing wall 30 is not longitudinally spaced more than 10 mm apart from the rear end 10a of the main absorbent region 10. More preferably, the rear end 30b of the leakage preventing wall 30 is located at the same longitudinal position as or rearward of the rear end 10a of the main absorbent region 10. Here, the front boundary point 46 is preferably at a distance of equal to or greater than 30 mm forward of the rear end 10a of the main absorbent region 10.

The leakage preventing wall 30 is transversely dimensioned such that when fully developed transversely outward and laid on the skin-side surface, the leakage preventing wall 30 may not project transversely outward beyond the front boundary point 46.

In the sanitary napkin 1 thus constructed, menstrual blood having diffused into the rear main absorbent region 10D may be absorbed in the high-density portions of the longitudinal compressed grooves 11, preventing farther transverse diffusion. Transverse leakage may be prevented with the leakage preventing walls 30 disposed on both sides of the rear main absorbent region 10D. Even if menstrual blood is directly given to the leakage preventing walls 30 and these leakage preventing walls 30 fall transversely outward, the relatively wide intermediate portion 42A of the rear flap 42 may effectively prevent adherence of the menstrual blood to the undergarment.

In the sanitary napkin 1, front pressure-sensitive adhesive layers 51, first rear pressure-sensitive adhesive layers 52, and second rear pressure-sensitive adhesive layers 53 are disposed on the garment-side surface, as shown in FIG. 2.

In the fold-back flap 41, the front pressure-sensitive adhesive layer 51 is disposed on the backsheet 5. The front pressure-sensitive adhesive layer 51 is of a rectangular shape and longitudinally extends over a given length with its center at the transverse reference line Ox—Ox.

In the rear flap 42, the first and second rear pressure-sensitive adhesive layers 52, 53 are disposed on the backsheet 5. The first rear pressure-sensitive adhesive layer 52 extends from the front spreading portion 42B to the intermediate portion 42A. The second rear pressure-sensitive adhesive layer 53 extends from the intermediate portion 42A to the rear converging portion 42D, and the second rear pressure-sensitive adhesive layer 53 has a rear end 53b rearward of the rear boundary point 47. Alternatively, the second rear pressure-sensitive adhesive layer 53 may be located exclusively in the rear converging portion 42D.

Here, the first rear pressure-sensitive adhesive layer 52 is of a larger area than the second rear pressure-sensitive adhesive layer 53, wherein the area ratio is 1.2 or more.

Since the first rear pressure-sensitive adhesive layer 52 is of a large area, the front portion of the rear flap 42 outside the leakage preventing wall 30 may be firmly fixed to the inner surface of the undergarment. On the other hand, the second rear pressure-sensitive adhesive layer 53 may be satisfactory as long as it has such a size as can exhibit an adhesive force capable of lightly fixing the rear flap 42 to the inner surface of the undergarment, at a position rearward of the rear end 30b of the leakage preventing wall 30.

Since the first and second rear pressure-sensitive adhesive layers 52, 53 are longitudinally separate from each other, the rear flap 42 may easily be adhered to the inner surface of the undergarment by merely pressing the front and rear portions of the rear flap 42, which facilitates attachment of the sanitary napkin 1 to the undergarment. In addition, since the total area of the first and second rear pressure-sensitive adhesive layers 52, 53 is not extremely large, the rear flap 42 may be prevented from adhering to the inner surface of the undergarment more strongly than is necessary, which facilitates detachment as well.

The first rear pressure-sensitive adhesive layer 52 is located forward of the rear end 30b of the leakage preventing wall 30. The first rear pressure-sensitive adhesive layer 52 has a front end 52a that is preferably at a distance of equal to or greater than 10 mm, more preferably at a distance of equal to or greater than 20 mm, forward of the rear end 30b. The first rear pressure-sensitive adhesive layer 52 is also located forward of the rear end 10a of the main absorbent region 10.

Figure 6:
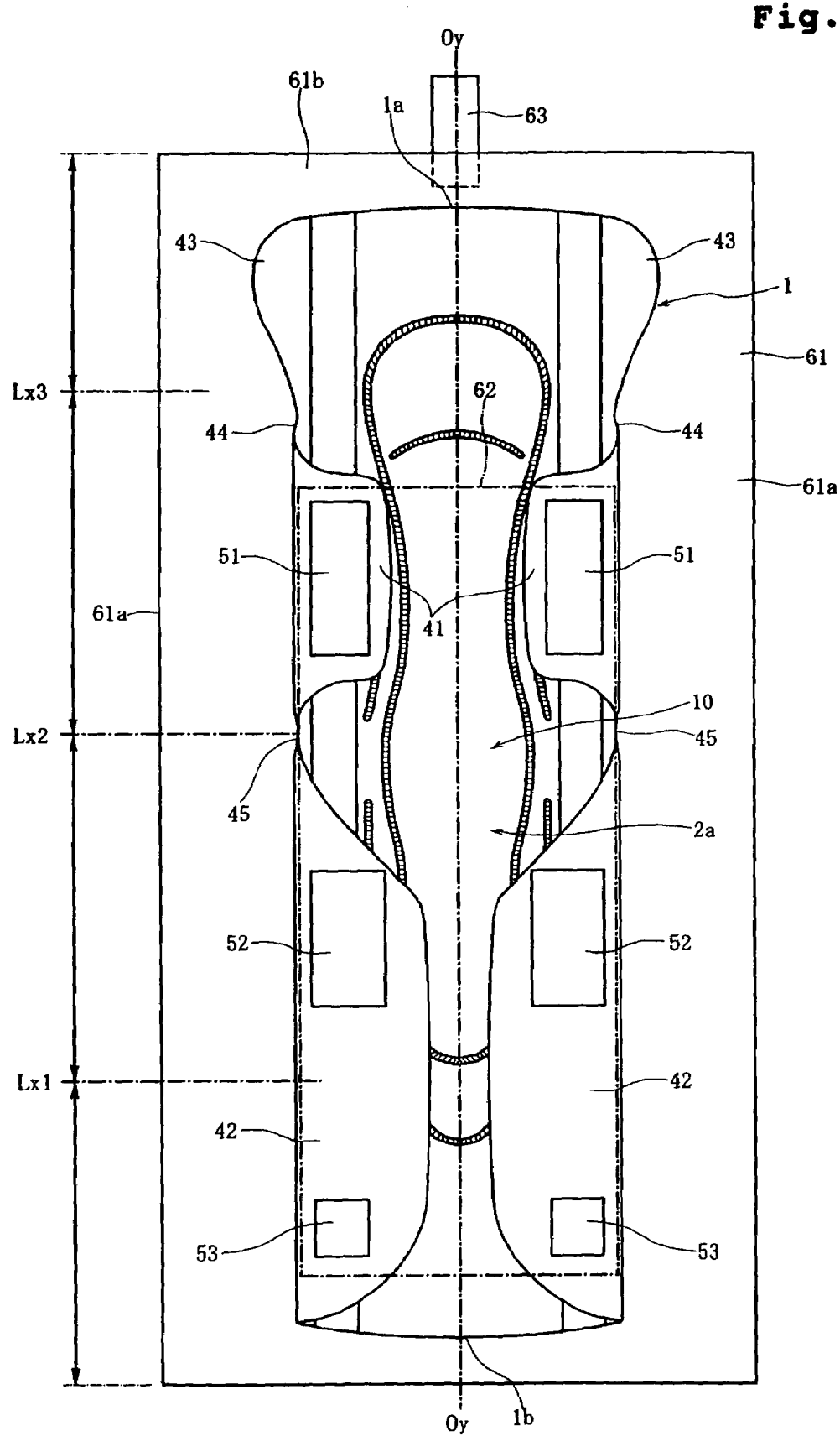
FIG. 6 is a top plan view showing how the sanitary napkin is individually packaged.

Here, when the individual rear flaps 42, 42 are folded back against the skin-side surface 2a to have the first and second rear pressure-sensitive adhesive layers 52, 53 directed toward the skin-side, as shown in FIG. 6, and the main body 2 is subsequently folded on a transversely extending folding line (folding boundary line) which bisects the length L1 of the intermediate portion 42A, the first rear pressure-sensitive adhesive layers 52 confront the second rear pressure-sensitive adhesive layers 53.

On the garment-side surface 2b of the main body 2, furthermore, central pressure-sensitive adhesive layers 54 are disposed on the right and left sides of the longitudinal centerline Oy—Oy. The central pressure-sensitive adhesive layers 54 are located inside the rising bases 31 of the leakage preventing walls 30 and extend longitudinally within the region of the liquid absorbent layer 6. The central pressure-sensitive adhesive layers 54 extend over the entire length of the main absorbent region 10 and beyond the front and rear ends 10b, 10a of the main absorbent region 10.

In the fold-back flap 41, as shown in FIGS. 2, 3 and 4, a reinforcing sheet 56 is interposed between and bonded to the backsheet 5 and the side sheet 4. Also in the rear flap 42, a reinforcing sheet 57 is interposed between and bonded to the backsheet 5 and the side sheet 4.

When folded back against the outer surface of the crotch part of the undergarment, the fold-back flap 41 thus reinforced with the reinforcing sheet 56 may be certainly fixed to the outer surface of the crotch part without twisting. The rear flap 42 in a developed state may also be fixed to the inner surface of the undergarment without twisting.

The reinforcing sheets 56, 57 may be formed of the same material to have the same thickness, or may be formed of different materials to have different thicknesses. Particularly when the reinforcing sheet 57 in the rear flap 42 is formed of a sheet capable of absorbing and retaining liquid, menstrual blood trying to ooze through between the side sheet 4 and the backsheet 5 can be retained by the reinforcing sheet 57.

When materials similar to the backsheet 5, the reinforcing sheet 56 or 57 and the side sheet 4 are stacked one on another, bonded to each other through a similar adhesive, cut into a sample of 65×65 mm, and then bent to a maximum curvature of $\pm 2.5$ $cm^{-1}$ with "Pure Bending Tester: KES-FB2" manufactured by Kato Tech Co., Ltd., the bending stiffness preferably falls within the range of 0.1 to 1.5 $mN \cdot cm^2/cm$, while the bending recovery preferably falls within the range of 0.03 to 1.5 $mN \cdot cm/cm$.

Here, the bending stiffness is a value obtained by differentiating a bending moment per 1 cm width of the sample with respect to the maximum curvature, while the bonding recovery is a difference in hysteresis curve between a bending moment when the sample is bent from one side to the maximum curvature and a bending moment when the sample is bent from the other side to the maximum curvature.

Within the foregoing ranges, the fold-back flaps 41 and the rear flaps 42 may hardly twist but may be soft enough to prevent an uncomfortable feeling.

Next, preferred examples of the individual components of the sanitary napkin 1 will be described.

The topsheet 3 is a liquid-permeable sheet, such as a through-air bonded nonwoven fabric, a spunlaced nonwoven fabric, or an apertured resin film (resin film formed with a large number of liquid passage holes). The backsheet 5 is a resin film that is impermeable to liquid but may be breathable.

The liquid absorbent layer 6 may be a layer of pulp, a layer of pulp and super absorbent polymer, or an air-laid nonwoven fabric in which only pulp or pulp and rayon are deposited by air-laid process and the fibers are fixed together through an adhesive. The liquid permeable layer 7 is a bulky nonwoven fabric of a three-dimensional network structure, such as a through-air bonded nonwoven fabric or an air-laid nonwoven fabric in which pulp and synthetic fibers are deposited by air-laid process and the fibers are fixed together through an adhesive.

The side sheet 4 is impermeable to liquid and is preferably treated to be water-repellent. The side sheet 4 may be a meltblown nonwoven fabric, a spunbonded nonwoven fabric, or a laminated composite of spunbond/meltblown/spunbond.

The side sheet 4, which forms the leakage preventing wall 30 and appears on the skin-side surface of the napkin outside the leakage preventing wall 30, preferably exerts some degree of frictional force against the wearer's skin. With such a frictional force, the rear flap 42 may hardly slip on the wearer's skin, so that even when the rear main absorbent region 10D is deformed to fit in the cleft of the buttocks, the rear flap 42 is hardly deformed to come closer to the longitudinal centerline Oy—Oy.

In order that the leakage preventing wall 30 and the rear flap 42 may have a good adhesion to the wearer's skin but may not give an uncomfortable feeling to the wearer's skin, the mean coefficient of surface friction preferably falls within the range of 0.2 to 0.7 when measured with "Surface Tester: KES-FB4" manufactured by Kato Tech Co., Ltd.

In order to provide the side sheet with such a surface friction coefficient, a meltblown nonwoven fabric made of ethylene alpha-olefin copolymer resin may be used for the side sheet 4, or a rubber-based hot-melt pressure-sensitive adhesive not containing a tackifier ingredient may be applied to the surface of the side sheet 4.

The reinforcing sheets 56, 57 may be of a spunbonded nonwoven fabric, a point-bonded nonwoven fabric, a meltblown nonwoven fabric, or a paper material. In order that the reinforcing sheet 57 in the rear flap 42 may exhibit the ability to absorb and retain liquid, the reinforcing sheet 57 may be of a pulp sheet, an absorbent paper manufactured by wet paper making process and then creped, an air-laid pulp in which pulp is deposited by air-laid process and then bonded together through an adhesive, or an air-laid nonwoven fabric in which pulp and thermoplastic synthetic fibers are deposited by air-laid process and then bonded together through an adhesive.

The pressure-sensitive adhesive layers 51, 52, 53 and 54 may be of a rubber-based hot-melt type adhesive.

The sanitary napkin 1 is to be worn with the intersection of the longitudinal centerline Oy—Oy and the transverse reference line Ox—Ox almost coinciding with the center of the woman's vaginal opening. Here, the fold-back flaps 41 projecting into the leg openings of the undergarment are folded back against the outer surface of the crotch part and adhered thereto through the front pressure-sensitive adhesive layers 51 disposed on the fold-back flaps 41. In addition, the garment-side surface 2b of the main body 2 of the sanitary napkin 1 is adhered to the inner surface of the undergarment, from the crotch part to the lower part of the back body, through the central pressure-sensitive adhesive layers 54.

Furthermore, the rear flaps 42 in a developed state are placed on the inner surface of the undergarment at the lower part of the back body and their garment-side surfaces are adhered to the inner surface of the undergarment through the first rear pressure-sensitive adhesive layers 52 and the second rear pressure-sensitive adhesive layers 53.

In the sanitary napkin 1, the skin-side surface 2a is recessed as shown in FIG. 1 due to the longitudinal elastic contractive force of the leakage preventing walls 30, whereby the leakage preventing walls 30 are raised from the skin-side surface 2a.

When worn, the longitudinal central portion of the front main absorbent region 10A, i.e., the intersection of the longitudinal centerline Oy—Oy and the transverse reference line Ox—Ox and its surrounding area may come into contact with the woman's vaginal opening, the intermediate portion between the front main absorbent region 10A and the intermediate main absorbent region 10B may confront the perineum, and the front portion of the intermediate main absorbent region 10B may confront the anus. Accordingly, the rear main absorbent region 10D may extend along the cleft of the buttocks and the rear portion of the rear main absorbent region 10D, i.e., the portion within about 5–20 mm forward from the rear end 10a of the main absorbent region 10 may confront the coccyx.

In the sanitary napkin 1, since the rear flap 42 has the intermediate portion 42A which extends over the length L1 with an almost constant width, the intermediate portion 42A extends alongside 50% or more of the length of the rear main absorbent region 10D. Accordingly, menstrual blood trying to flow rearward along the skin-side surface 2a or posteriorly down the wearer's skin can be certainly blocked by the leakage preventing walls 30 and the intermediate portions 42A disposed on both sides of the rear main absorbent region 10D, decreasing the probability that menstrual blood will leak out of the rear flaps 42 to leave a stain on the undergarment.

The first rear pressure-sensitive adhesive layer 52, which extends alongside the rear main absorbent region 10D from the intermediate portion 42A to the front spreading portion 42B in the rear flap 42, preferably has an area of 400 to 1000 cm$^2$. Within this range, the rear flap 42 may be firmly fixed, from the intermediate portion 42A to the front spreading portion 42B, to the inner surface of the undergarment. Furthermore, the rear flap 42 may also be firmly fixed at a position forward of the rear end 30b of the leakage preventing wall 30.

When the intermediate main absorbent region 10B and the rear main absorbent region 10D confront the anus and the cleft of the buttocks, a tightening force of the undergarment tends to deform the rear main absorbent region 10D to fit in the cleft of the buttocks. In this region, accordingly, the liquid absorbent layer 6 may be deformed to project toward the wearer's body. At this time, the whole liquid absorbent layer 6 may be subjected to a force which tries to reduce the width. However, since the front portion of the rear flap 42 can be firmly fixed to the undergarment through the first rear pressure-sensitive adhesive layer 52, the liquid absorbent layer 6 can be effectively prevented from being deformed to significantly reduce the width. As a result, the sanitary napkin 1 may hardly be deformed to bring the rising bases 31 of the leakage preventing walls 30 closer to the cleft of the buttocks, and in addition, the leakage preventing walls 30 can be prevented from falling to cover a large area of the rear main absorbent region 10D.

Menstrual blood discharged from the vaginal opening may pass through the topsheet 3 and the liquid permeable layer 7 mainly in the front main absorbent region 10A for subsequent absorption by the liquid absorbent layer 6. Should menstrual blood flow down the surface of the topsheet 3 to migrate rearward, the rear main absorbent region 10D of a sufficiently large area can collect such menstrual blood. Even if menstrual blood flowing posteriorly down the wearer's body during sleep comes into direct contact with the leakage preventing wall 30, the relatively wide intermediate portion 42A of the rear flap 42 outside the wall 30 can effectively prevent the menstrual blood from leaking out to leave a stain on the undergarment.

When a wearer lies on her back during sleep, on the other hand, a portion rearward of the intermediate main absorbent region 10B will be pressed and flattened by the buttocks, so that the sanitary napkin 1 may be folded at the intermediate main absorbent region 10B located between the front main absorbent region 10A that is in close contact with the wearer's crotch and the flattened portion or at a portion forward of the region 10B, easily forming a space between the folded portion and the wearer's body. However, since the leakage preventing walls 30 are prevented from easily coming closer to the center and can easily be kept in the rising position, the space may be blocked by the leakage preventing walls 30 kept in the rising position.

In this case, even if menstrual blood flowing posteriorly down the wearer's body comes into direct contact with and goes beyond the leakage preventing wall 30 to flow obliquely rearward as indicated by the arrow (i) in FIG. 5, the menstrual blood hardly reaches the inner surface of the undergarment due to the presence of the intermediate portion 42A of the rear flap 42.

FIG. 6 shows one example of how to form a package in which the sanitary napkin 1 is individually packaged.

In FIG. 6, the sanitary napkin 1 is mounted with the garment-side surface 2b opposed to a packaging sheet 61. Here, the central pressure-sensitive adhesive layers 54 disposed on the garment-side surface 2b are covered with a release sheet that is firmly fixed to the packaging sheet 61. Alternatively, the packaging sheet 61 may have a surface subjected to a release treatment so that the central pressure-sensitive adhesive layers 54 can be directly adhered to the packaging sheet 61.

In the sanitary napkin 1, the individual fold-back flaps 41 are folded back against the skin-side surface 2a to direct the front pressure-sensitive adhesive layers 51 upward and the individual rear flaps 42 are also folded back against the skin-side surface 2a to direct the first and second rear pressure-sensitive adhesive layers 52, 53 upward.

The front pressure-sensitive adhesive layers 51 and the first and second rear pressure-sensitive adhesive layers 52, 53 thus directed upward are covered with a single rectangular release sheet 62 (shown with a chain line). The release sheet 62 is not bonded to but separate from the packaging sheet 61.

Furthermore, the sanitary napkin 1, as well as the packaging sheet 61, may be first folded on a folding boundary line Lx1 with the skin-side surface 2a directed inward, secondly folded on a folding boundary line Lx2 with the skin-side surface 2a directed inward, and thirdly folded on a folding boundary line Lx3. Then, a lead tape 63 extending from the front end of the packaging sheet 61 may be adhered to the outer surface of the packaging sheet 61. Moreover, the packaging sheet 61 may be heat-sealed along side edge portions 61a, 61a.

The folding boundary line Lx2 is preferably located forward of the first rear pressure-sensitive adhesive layers 52 so as not to cross it. The folding boundary line Lx1 is preferably located between the first and second rear pressure-sensitive adhesive layers 52, 53 so as not to cross any of the rear pressure-sensitive adhesive layers 52, 53. The folding boundary line Lx3 is preferably located forward of the front pressure-sensitive adhesive layers 51 so as not to cross it. If the folding boundary lines do not cross the pressure-sensitive adhesive layers, the pressure-sensitive adhesive layers will not be creased when the sanitary napkin is in a packaged state. Therefore, the individual pressure-sensitive adhesive layers in the sanitary napkin after unwrapped can be effectively prevented from being folded back and adhered to itself.

The folding boundary line Lx2 is preferably located forward of the second starting point 45 so as not to cross the area between the second starting point 45 and the front boundary point 46, i.e., the front spreading portion 42B. If the folding boundary line Lx2 is located between the second starting point 45 and the front boundary point 46, the folding boundary line Lx2 is preferably located closer to the second starting point 45 than to the midpoint between the second starting point 45 and the front boundary point 46.

With this construction, a troublesome crease will not be formed in the front spreading portion 42B when the sanitary napkin is in a packaged state, so that when unwrapped, the developed front spreading portion 42B may be flat. Accordingly, the rear flap 42 may easily be kept developed on the inner surface of the undergarment so as not to be folded or wrinkled.

When the sanitary napkin 1 is to be used, the packaging sheet 61, as well as the sanitary napkin 1, may be developed into the state of FIG. 6. Then, the packaging sheet 61 may be peeled off from the garment-side surface 2b of the sanitary napkin 1, resulting in a state where the fold-back flaps 41 and the rear flaps 42 are kept in a folded-back state with the release sheet 62. Subsequently, the central pressure-sensitive adhesive layers 54 may be adhered to the inner surface of the undergarment from the crotch part to the back body, and thereafter, the release sheet 62 may be peeled off and the fold-back flaps 41 may be folded back against and adhered to the outer surface of the crotch part of the undergarment. Here, the rear flaps 42 after developed may be certainly adhered to the inner surface of the back body of the undergarment through the first and second rear pressure-sensitive adhesive layers 52, 53 only by pressing front and rear portions thereof.

When the sanitary napkin is to be disposed of after use, on the other hand, the rear flaps 42 may be first folded back against the skin-side surface 2a and then folded on a transversely extending line coinciding with the midpoint between the front boundary point 46 and the rear boundary point 47 (i.e., midpoint of the parallel line of the length L1), so that they can stay in such a folded state with the first rear pressure-sensitive adhesive layers 52 being opposed and adhered to the second rear pressure-sensitive adhesive layers 53. In addition, the fold-back flaps 41 may be folded back against the skin-side surface 2a and then the main body 2 may be folded near the folding boundary line Lx2 shown in FIG. 6, whereby the front pressure-sensitive adhesive layers 51 can be adhered to the backsheet 5. Thus, the sanitary napkin 1 after use may be folded up compactly and maintained in the folded state, facilitating disposal.

Figure 7:
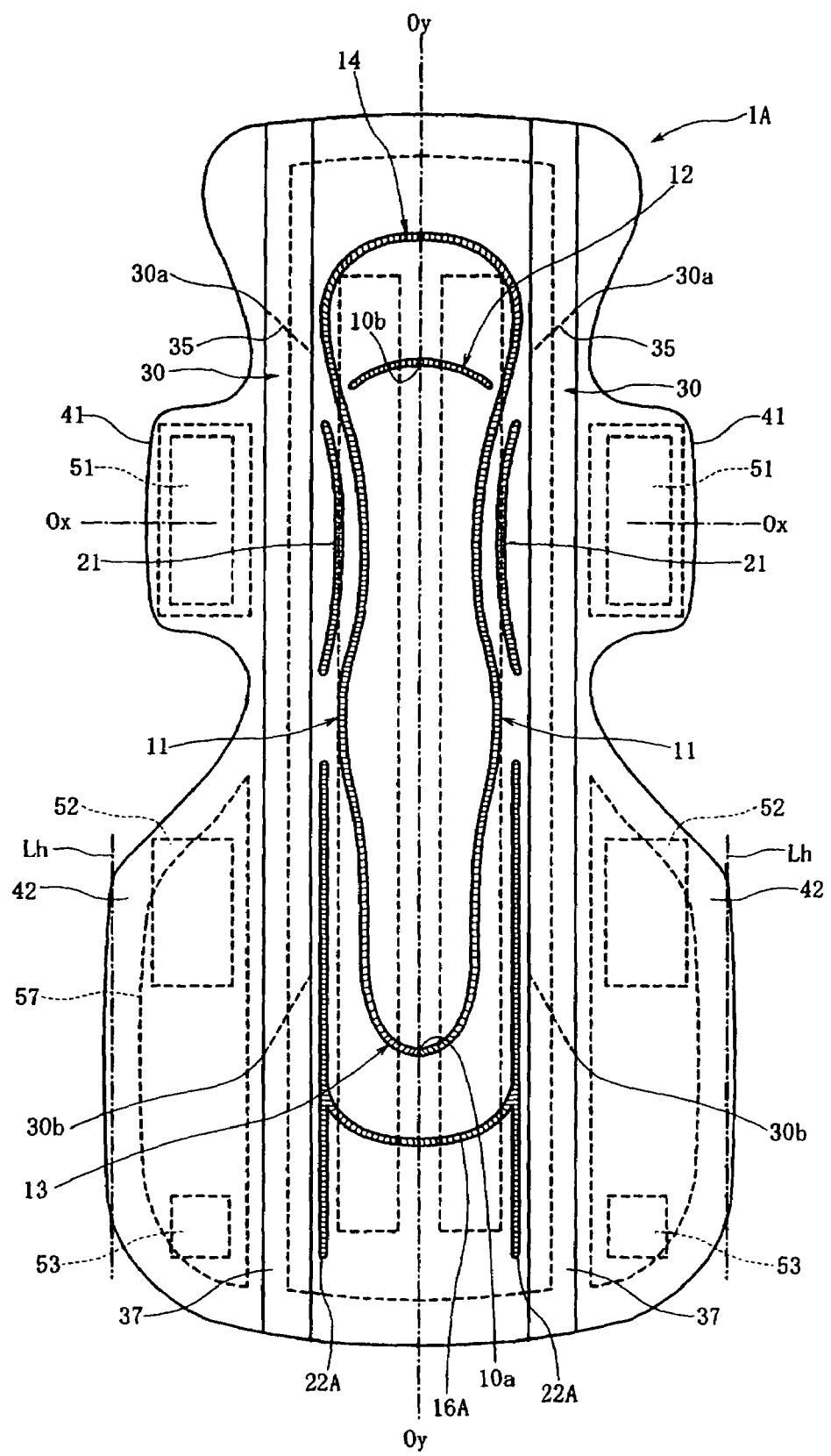
FIG. 7 is a top plan view of a sanitary napkin according to a second embodiment of the present invention.

FIG. 7 is a top plan view showing a sanitary napkin 1A according to a second embodiment of the present invention.

The sanitary napkin 1A is similar to the sanitary napkin 1 shown in FIG. 2, except that the pattern of the compressed grooves formed in the skin-side surface 2a is modified only partially.

The difference is such that a rear outside compressed groove 16A disposed rearward of the rear transverse compressed groove 13 is formed to connect second outside longitudinal compressed grooves 22A, 22A disposed outside thereof, as shown in FIG. 7. The remaining constructions, preferred dimensions, and preferred dimensional relationships are not changed from those in the sanitary napkin 1.

Figure 8:
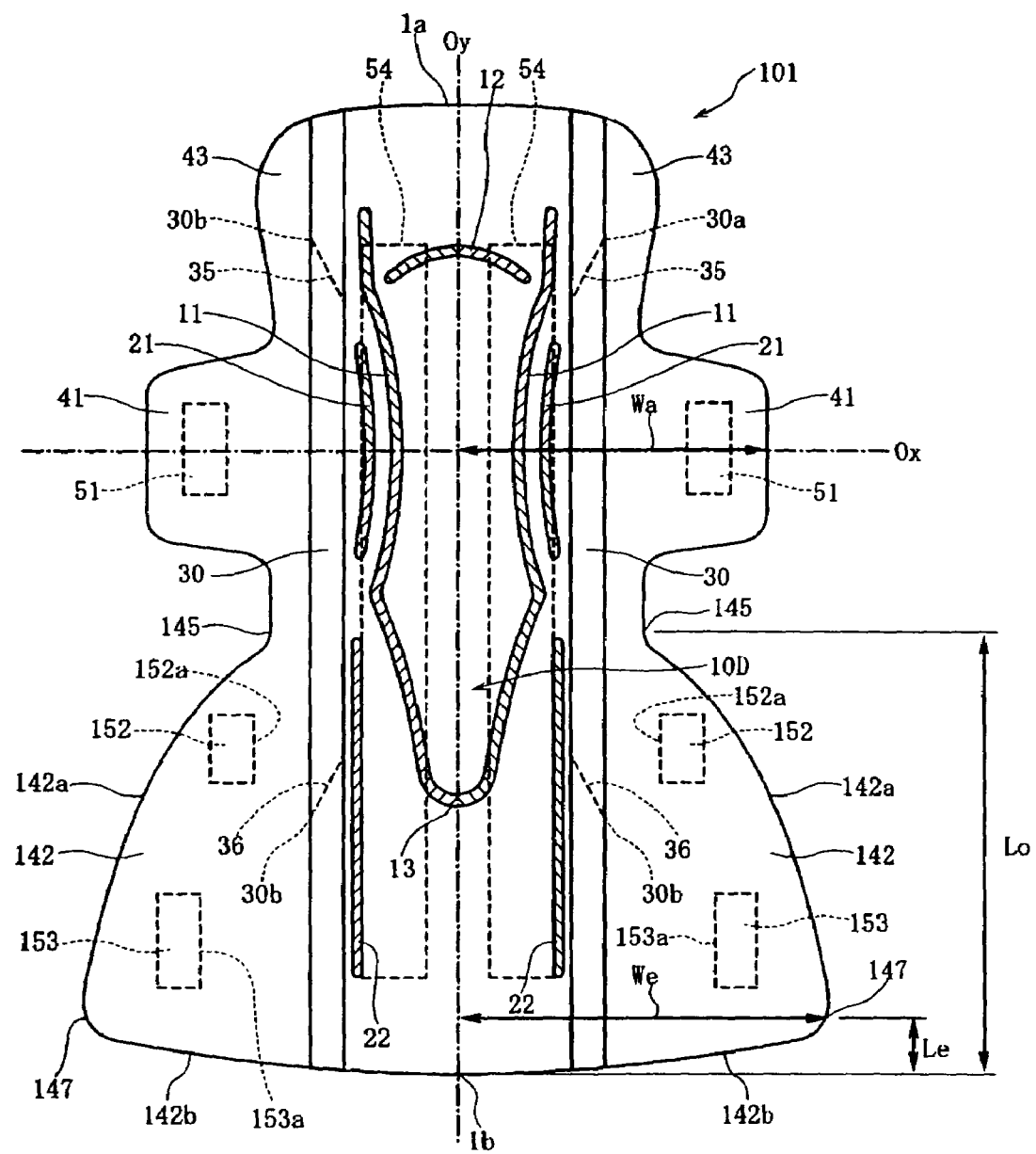
FIG. 8 is a top plan view of a sanitary napkin according to a third embodiment of the present invention.

FIG. 8 is a top plan view showing a sanitary napkin 101 according to a third embodiment of the present invention. The sanitary napkin 101 has rear flaps 142 that differ from the rear flaps 42 of the first embodiment in shape. Hereinbelow, the detailed description of the portions having the same or substantially the same constructions, shapes and dimensional relationships as those of the first embodiment will be omitted by designating them by the common reference numerals.

The rear flap 142 of the sanitary napkin 101 gradually increases the half-width from a second starting point 145 toward the rear end edge 1b of the napkin, so that the rear flaps 142 has a side edge 142a that is outwardly curved with a relatively large radius of curvature.

In the rear portion of the rear flap 142 is provide a boundary point 147 where the radius of curvature is reduced. At the boundary point 147, the sanitary napkin has a widest portion of a largest half-width We. The half-width We may be equal to or greater than the half-width Wa.

The rear flap 142 also has a rear edge 142b where the half-width rapidly decreases rearward from the boundary point 147. In the embodiment shown in FIG. 8, the rear edge 142b is on an extension of the rear end edge 1b of the napkin, wherein the rear end edge 1b and the rear edge 142b form an outwardly curved edge whose curvature is almost constant.

In the sanitary napkin 101, the boundary point 147 where the width of the rear flap 142 becomes largest is located close to the rear end edge 1b, wherein a length Le from the boundary point 147 to the rear end edge 1b of the napkin may be at most 1/3, preferably at most 1/5 of the length L0 of the rear flap 142.

On the garment-side surface of the rear flap 142, a first rear pressure-sensitive adhesive layer 152 is disposed forward of the rear end 30b of the leakage preventing wall 30, and a second rear pressure-sensitive adhesive layer 153 is disposed rearward of the first rear pressure-sensitive adhesive layer 152.

The second rear pressure-sensitive adhesive layer 153 is located close to the boundary point 147, and the second rear pressure-sensitive adhesive layer 153 is located farther away from the longitudinal centerline Oy—Oy than is the first rear pressure-sensitive adhesive layer 152. That is, the distance from the longitudinal centerline Oy—Oy to an inner edge 153a of the second rear pressure-sensitive adhesive layer 153 is greater than the distance from the longitudinal centerline Oy—Oy to an inner edge 152a of the first rear pressure-sensitive adhesive layer 152.

In the sanitary napkin 101, the longitudinal compressed grooves 11, the front transverse compressed groove 12 and the rear transverse compressed groove 13 are slightly different in shape from those in the first embodiment shown in FIG. 2, but their functions remain unchanged.

Figure 9:
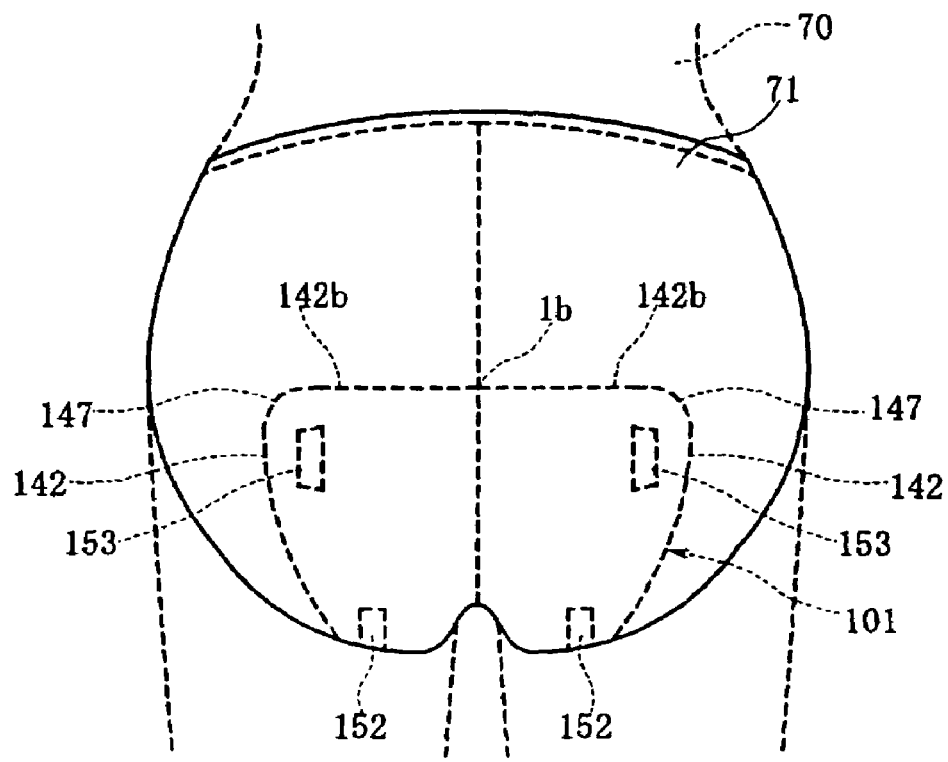
FIG. 9 is a view showing a state where the sanitary napkin according to the third embodiment is worn.

FIG. 9 is an explanatory diagram showing a state where the sanitary napkin 101 is fixed on a body 70 along with an undergarment 71 from the side of the buttocks of the body 70.

In the sanitary napkin 101, as described above, the rear flap 142 gradually increases the half-width toward the rear end edge 1b to provide the widest portion near the rear end edge 1b. Therefore, when the rear flaps 142 are widely opened on the inner surface of the back body of the undergarment 71, the boundary points 147 may be located close to the waist part of the undergarment 71.

Accordingly, when the undergarment 71 is put on along with the sanitary napkin 101 fixed thereto, the boundary points 147 close to the waist part of the undergarment 71 can easily be pulled obliquely upward, whereby the rear flaps 142 can be applied to the body 70 in a fully opened state.

Moreover, since the second rear pressure-sensitive adhesive layers 153 are located close to the boundary points 147, the rear flaps 142 can be firmly fixed, near the widest portion, to the undergarment 71. Therefore, the rear flaps 142 of the sanitary napkin 101 can be stabilized on the back body of the undergarment 71 without twisting or curling.

Since the first rear pressure-sensitive adhesive layers 152 are located forward of the rear ends 30b of the leakage preventing walls 30, the leakage preventing walls 30, as well as the rear main absorbent region 10D, can be stabilized in positions facing the cleft of the buttocks. When a wearer lies on her back during sleep, on the other hand, menstrual blood trying to migrate rearward of the sanitary napkin 101 can be received by the rear flaps 142, preventing outward leakage of menstrual blood.

Figure 10:
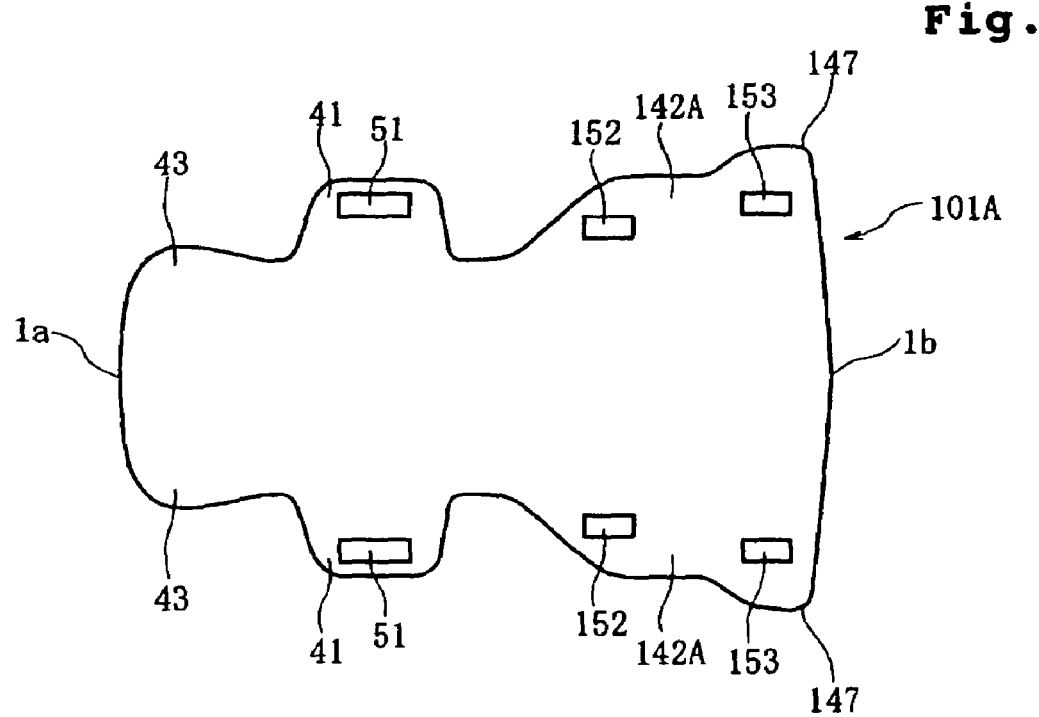
FIG. 10 is a bottom plan view showing a modification of the sanitary napkin according to the third embodiment.
Figure 11:
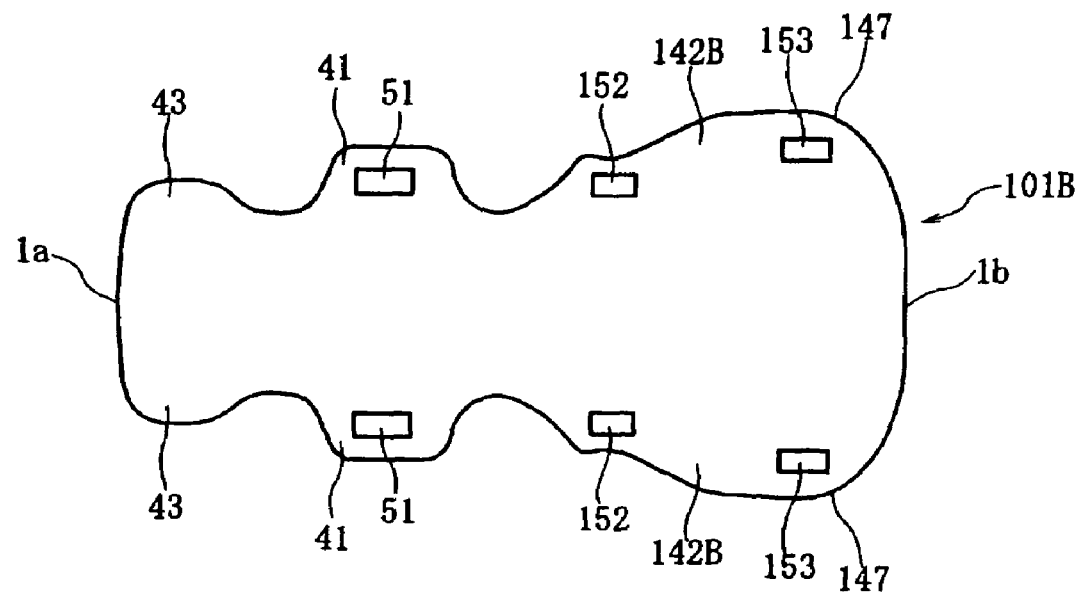
FIG. 11 is a bottom plan view showing another modification of the sanitary napkin according to the third embodiment.
Figure 12:
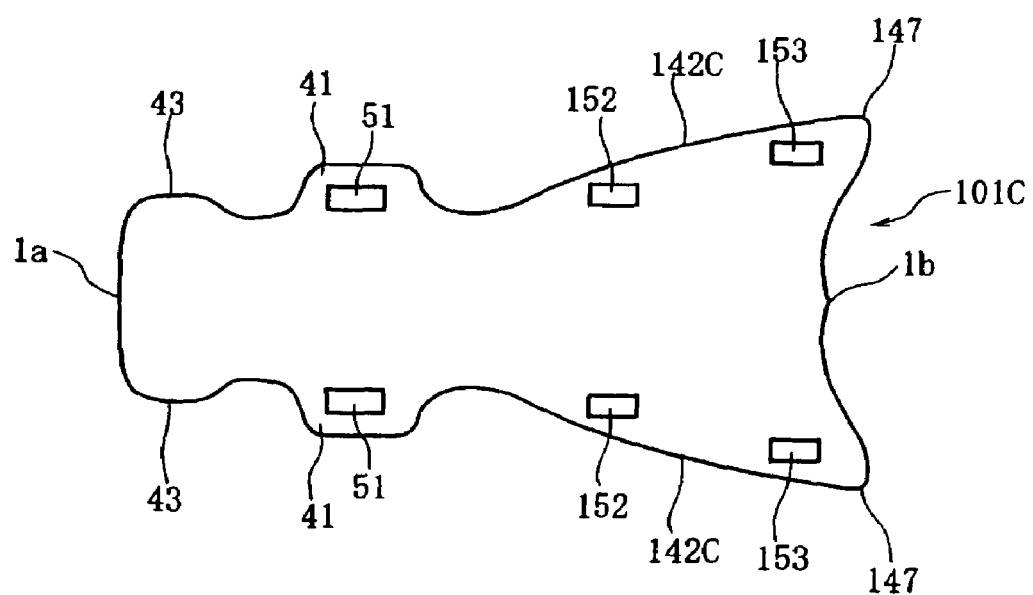
FIG. 12 is a bottom plan view showing still another modification of the sanitary napkin according to the third embodiment.

FIGS. 10, 11 and 12 are bottom plan views showing modifications of the third embodiment from the garment-side. Here, the central pressure-sensitive adhesive layers 54 are omitted from the drawings.

FIG. 10 shows a sanitary napkin 101A having rear flaps 142A; FIG. 11 shows a sanitary napkin 101B having rear flaps 142B. In each napkin, the edge of the rear flap is wavy, i.e., shaped to stepwise increase the width. Here, the boundary points 147 where the rear flaps provide the widest portion are located close to the rear end edge 1b.

FIG. 12 shows a sanitary napkin 101C having rear flaps 142C, wherein the boundary points 147 are located rearward of the rear end edge 1b. Therefore, when the sanitary napkin 101C is fixed on the inner surface of the undergarment, the boundary points 147 can easily be pulled obliquely upward.

According to the present invention, as has been described hereinabove, the rear flaps can be firmly fixed to an inner surface of an undergarment, effectively preventing deformation of the liquid absorbent layer, which would otherwise bring the leakage preventing walls closer to each other, and increasing the effect of preventing liquid leakage in the transverse direction.

Although the present invention has been illustrated and described with respect to exemplary embodiments thereof, it should be understood by those skilled in the art that the foregoing and various other changes, omission and additions may be made therein and thereto, without departing from the spirit and scope of the present invention. Therefore, the present invention should not be understood as limited to the specific embodiments set out above but to include all possible embodiments which can be embodied within a scope encompassed and equivalent thereof with respect to the features set out in the appended claims.

What is claimed is:

1. A sanitary napkin comprising:
    an elongated main body having an skin-side surface and a garment-side surface and including a liquid absorbent layer for absorbing liquid applied to the skin-side surface and a backsheet appearing on the garment-side surface;
    fold-back flaps configured to be folded back against an outer surface of an undergarment at a crotch part thereof in use, the fold-back flaps projecting outward from transversely opposite sides of the main body and having front pressure-sensitive adhesive layers on garment-side surfaces thereof for adhering the fold-back flaps to the outer surface of the undergarment;
    rear flaps configured to be placed on an inner surface of the undergarment in use in an unfolded state, the rear flaps projecting outward from the transversely opposite sides of the main body and having rear pressure-sensitive adhesive layers on garment-side surfaces thereof for adhering the rear flaps to the inner surface of the undergarment, the rear flaps being located rearward of the fold-back flaps and longer in length than the fold-back flaps; and
    longitudinally extending leakage preventing walls disposed on the skin-side surface of the main body and at equal distances on each side of a longitudinal centerline, each leakage preventing wall having front and rear ends fixed to the skin-side surface, said front end spaced away from the longitudinal frontal edge of the main body and said rear end spaced away from the longitudinal rear edge of the main body, and a plurality of elastic members extending longitudinally an entire length of the leakage preventing wall and for exhibiting an elastic contractive force to bring the front and rear ends of the leakage preventing wall closer to each other so as to rise from the skin-side surface,
    wherein the rear pressure-sensitive adhesive layers are separately located forward and rearward from the rear ends of the leakage preventing walls.

2. A sanitary napkin according to claim 1, wherein on each side of the longitudinal centerline, a front end of the rear pressure-sensitive adhesive layer is at a distance of equal to or greater than 10 mm forward of the rear end of the leakage preventing wall.

3. A sanitary napkin according to claim 1, wherein on each side of the longitudinal centerline, a starting point from which a half-width, measured from the longitudinal centerline to a side edge, starts to increase rearward is located rearward of the fold-back flap, and the rear flap includes: a front spreading portion where the half-width gradually increases rearward from the starting point; an intermediate portion where the side edge extends parallel to the longitudinal centerline or extends with a deviation within a range of ±5 mm transversely from an imaginary line parallel to the longitudinal centerline; and a rear converging portion where the half-width gradually decreases toward a rear end edge of the napkin, wherein a front boundary point between the front spreading portion and the intermediate portion is located forward of the rear end of the leakage preventing wall.

4. A sanitary napkin according to claim 3, wherein the front boundary point is at a distance of equal to or greater than 30 mm forward of the rear end of the leakage preventing wall.

5. A sanitary napkin according to claim 3, wherein both a width from a rising base of the leakage preventing wall to the front boundary point and a width from the rising base to the rear boundary point fall within the range of 30 to 70 mm.

6. A sanitary napkin according to claim 3, wherein a length from a transverse reference line, which longitudinally bisects the fold-back flap, to the front boundary point falls within the range of 80 to 150 mm.

7. A sanitary napkin according to claim 3, wherein the skin-side surface of the main body has an elongated main absorption region surrounded by a compressed groove in a region between the leakage preventing walls, and the front boundary point is at a distance of equal to or greater than 30 mm forward of a rear end of the main absorption region.

8. A sanitary napkin according to claim 3, wherein auxiliary pressure-sensitive adhesive layers are further disposed on the garment-side surfaces of the rear flaps at a distance rearward of the rear pressure-sensitive adhesive layers, wherein
    on each side of the longitudinal centerline, a front end of the rear pressure-sensitive adhesive layer is located forward of the front boundary point, and a rear end of the auxiliary pressure-sensitive adhesive layer is located rearward of the rear boundary point.

9. A sanitary napkin according to claim 8, wherein the individual rear flaps are configured to be folded back against the skin-side surface of the main body and the main body is also configured to be folded, with the skin-side surface directed inward, on a transversely extending folding boundary line coinciding with a midpoint between the front boundary point and the rear boundary point, wherein
    the folding boundary line crosses none of the pressure-sensitive adhesive layers, and when the individual rear flaps are folded back and the main body is subsequently folded on the folding boundary line, the rear pressure-sensitive adhesive layers confront the auxiliary pressure-sensitive adhesive layers.

10. A sanitary napkin according to claim 1, wherein a half-width, measured from the longitudinal centerline to a side edge, is larger in a rear portion of the rear flap than in a front portion of the rear flap, and is largest rearward of a longitudinal center of the rear flap.

11. A sanitary napkin comprising:
an elongated main body having a skin-side surface and a garment-side surface and including a liquid absorbent layer for absorbing liquid applied to the skin-side surface and a backsheet appearing on the garment-side surface;
fold-back flaps configured to be folded back against an outer surface of an undergarment at a crotch part thereof in use, the fold-back flaps projecting outward from transversely opposite sides of the main body and having front pressure-sensitive adhesive layers on garment-side surfaces thereof for adhering the fold-back flaps to the outer surface of the undergarment;
rear flaps configured to be placed on an inner surface of the undergarment in use in an unfolded state, the rear flaps projecting outward from the transversely opposite sides of the main body and having rear pressure-sensitive adhesive layers on garment-side surfaces thereof for adhering the rear flaps to the inner surface of the undergarment, the rear flaps being located rearward of the fold-back flaps and larger in length than the fold-back flaps; and
longitudinally extending leakage preventing walls disposed on the skin-side surface of the main body and at equal distances on each side of a longitudinal centerline, each leakage preventing wall having front and rear ends fixed to the skin-side surface and exhibiting an elastic contractive force to bring the front and rear ends closer to each other so as to rise from the skin-side surface,
wherein the rear pressure-sensitive adhesive layers are located forward of the rear ends of the leakage preventing walls,
wherein on each side of the longitudinal centerline, a starting point from which a half-width, measured from the longitudinal centerline to a side edge, starts to increase rearward is located rearward of the fold-back flap, and the rear flap includes: a front spreading portion where the half-width gradually increases rearward from the starting point; an intermediate portion where the side edge extends parallel to the longitudinal centerline or extends with a deviation within a range of ±5 mm transversely from an imaginary line parallel to the longitudinal centerline; and a rear converging portion where the half-width gradually decreases toward a rear end edge of the napkin, wherein a front boundary point between the front spreading portion and the intermediate portion is located forward of the rear end of the leakage preventing wall,
wherein L1/L0 is at least ⅓, where L0 represents a length from the starting point to the rear end edge of the napkin while L1 represents a length from the front boundary point to a rear boundary point between the intermediate portion and the rear converging portion.

12. A sanitary napkin according to claim 11, wherein L1 falls within the range of 60 to 200 mm.

13. A sanitary napkin comprising:
an elongated main body having a skin-side surface and a garment-side surface and including a liquid absorbent layer for absorbing liquid applied to the skin-side surface and a backsheet appearing on the garment-side surface;
fold-back flaps configured to be folded back against an outer surface of an undergarment at a crotch part thereof in use, the fold-back flaps projecting outward from transversely opposite sides of the main body and having front pressure-sensitive adhesive layers on garment-side surfaces thereof for adhering the fold-back flaps to the outer surface of the undergarment;
rear flaps configured to be placed on an inner surface of the undergarment in use in an unfolded state, the rear flaps projecting outward from the transversely opposite sides of the main body and having rear pressure-sensitive adhesive layers on garment-side surfaces thereof for adhering the rear flaps to the inner surface of the undergarment, the rear flaps being located rearward of the fold-back flaps and larger in length than the fold-back flaps; and
longitudinally extending leakage preventing walls disposed on the skin-side surface of the main body and at equal distances on each side of a longitudinal centerline, each leakage preventing wall having front and rear ends fixed to the skin-side surface and exhibiting an elastic contractive force to bring the front and rear ends closer to each other so as to rise from the skin-side surface,
wherein the rear pressure-sensitive adhesive layers are located forward of the rear ends of the leakage preventing walls,
wherein on each side of the longitudinal centerline, a starting point from which a half-width, measured from the longitudinal centerline to a side edge, starts to increase rearward is located rearward of the fold-back flap, and the rear flap includes: a front spreading portion where the half-width gradually increases rearward from the starting point; an intermediate portion where the side edge extends parallel to the longitudinal centerline or extends with a deviation within a range of ±5 mm transversely from an imaginary line parallel to the longitudinal centerline; and a rear converging portion where the half-width gradually decreases toward a rear end edge of the napkin, wherein a front boundary point between the front spreading portion and the intermediate portion is located forward of the rear end of the leakage preventing wall,
wherein an imaginary line, which coincides with the starting point and is tangent to an edge of the rear flap, forms an angle of 30 to 45 degrees with the longitudinal centerline.

14. A sanitary napkin comprising:
an elongated main body having a skin-side surface and a garment-side surface and including a liquid absorbent layer for absorbing liquid applied to the skin-side surface and a backsheet appearing on the garment-side surface;
fold-back flaps configured to be folded back against an outer surface of an undergarment at a crotch part thereof in use, the fold-back flaps projecting outward from transversely opposite sides of the main body and having front pressure-sensitive adhesive layers on garment-side surfaces thereof for adhering the fold-back flaps to the outer surface of the undergarment;
rear flaps configured to be placed on an inner surface of the undergarment in use in an unfolded state, the rear flaps projecting outward from the transversely opposite sides of the main body and having rear pressure-sensitive adhesive layers on garment-side surfaces thereof for adhering the rear flaps to the inner surface of the undergarment, the rear flaps being located rearward of the fold-back flaps and larger in length than the fold-back flaps; and longitudinally extending leakage preventing walls disposed on the skin-side surface of the main body and at equal distances on each side of a longitudinal centerline, each leakage preventing wall having front and rear ends fixed to the skin-side surface and exhibiting an elastic contractive force to bring the front and rear ends closer to each other so as to rise from the skin-side surface, wherein the rear pressure-sensitive adhesive layers are located forward of the rear ends of the leakage preventing walls, wherein a half-width, measured from the longitudinal centerline to a side edge, is larger in a rear portion of the rear flap than in a front portion of the rear flap, and is largest rearward of a longitudinal center of the rear flap, wherein $Le/L0$ is at most $\frac{1}{5}$, where $Le$ represents a length from a point where the half-width is largest to a rear end edge of the napkin while $L0$ represents a length of the rear flap.

15. A sanitary napkin comprising:

an elongated main body having a skin-side surface and a garment-side surface and including a liquid absorbent layer for absorbing liquid applied to the skin-side surface and a backsheet appearing on the garment-side surface;

fold-back flaps configured to be folded back against an outer surface of an undergarment at a crotch part thereof in use, the fold-back flaps projecting outward from transversely opposite sides of the main body and having front pressure-sensitive adhesive layers on garment-side surfaces thereof for adhering the fold-back flaps to the outer surface of the undergarment;

rear flaps configured to be placed on an inner surface of the undergarment in use in an unfolded state, the rear flaps projecting outward from the transversely opposite sides of the main body and having rear pressure-sensitive adhesive layers on garment-side surfaces thereof for adhering the rear flaps to the inner surface of the undergarment, the rear flaps being located rearward of the fold-back flaps and larger in length than the fold-back flaps; and longitudinally extending leakage preventing walls disposed on the skin-side surface of the main body and at equal distances on each side of a longitudinal centerline, each leakage preventing wall having front and rear ends fixed to the skin-side surface and exhibiting an elastic contractive force to bring the front and rear ends closer to each other so as to rise from the skin-side surface, wherein the rear pressure-sensitive adhesive layers are located forward of the rear ends of the leakage preventing walls, wherein a half-width, measured from the longitudinal centerline to a side edge, is larger in a rear portion of the rear flap than in a front portion of the rear flap, and is largest rearward of a longitudinal center of the rear flap, wherein auxiliary pressure-sensitive adhesive layers are further disposed on the garment-side surfaces of the rear flaps at a distance rearward of the rear pressure-sensitive adhesive layers, wherein the auxiliary pressure-sensitive adhesive layers are farther away from the longitudinal centerline than is the rear pressure-sensitive adhesive layers.

* * * * *